United States Patent [19]

Ichijima et al.

[11] Patent Number: 4,526,861
[45] Date of Patent: Jul. 2, 1985

[54] SILVER HALIDE COLOR PHOTOGRAPHIC LIGHT-SENSITIVE MATERIAL COMPRISING COUPLER HAVING NITROGEN-CONTAINING HETEROCYCLIC RING

[75] Inventors: Seiji Ichijima; Takeshi Hirose, both of Kanagawa, Japan

[73] Assignee: Fuji Photo Film Co., Ltd., Kanagawa, Japan

[21] Appl. No.: 593,795

[22] Filed: Mar. 27, 1984

[30] Foreign Application Priority Data

Mar. 29, 1983 [JP] Japan .................................. 58-54742

[51] Int. Cl.³ .......................... G03C 7/32; G03C 7/26; G03C 7/00; G03C 1/40
[52] U.S. Cl. .................................... 430/385; 430/553; 430/555; 430/557; 430/558
[58] Field of Search ............... 430/553, 555, 557, 558, 430/385

[56]  References Cited

U.S. PATENT DOCUMENTS

| | | | |
|---|---|---|---|
| 4,057,432 | 11/1977 | Fujiwhara et al. | 430/558 X |
| 4,124,396 | 11/1978 | Osborn | 430/553 |
| 4,269,936 | 5/1981 | Arai et al. | 430/558 X |
| 4,289,847 | 9/1981 | Ishikawa et al. | 430/557 X |
| 4,352,873 | 10/1982 | Toda et al. | 430/558 X |
| 4,356,258 | 10/1982 | Usui et al. | 430/558 X |
| 4,368,257 | 1/1983 | Usagawa et al. | 430/558 X |
| 4,404,274 | 9/1983 | Arai et al. | 430/558 X |

FOREIGN PATENT DOCUMENTS 747628  4/1956  United Kingdom ................ 430/553

*Primary Examiner*—John E. Kittle
*Assistant Examiner*—Mukund J. Shah
*Attorney, Agent, or Firm*—Sughrue, Mion, Zinn, Macpeak and Seas

[57] ABSTRACT

A silver halide color photographic light-sensitive material comprising a support having thereon at least one silver halide emulsion layer, the color photographic light-sensitive material containing a coupler having a group represented by the general formula (I)

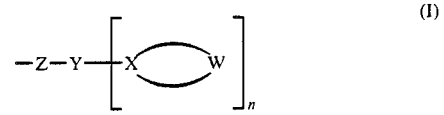

wherein W represents

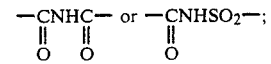

represents an organic residue necessary for forming a 5-membered or 6-membered nitrogen-containing heterocyclic ring or a condensed ring thereof together with W; Y represents an organic residue connecting Z and X and containing at least one carbon atom which is bonded to Z; Z represents an oxygen atom or a sulfur atom; and n represents an integer of 1 to 2; at the coupling position of the coupler and a method of forming a color image using the silver halide color photographic light-sensitive material. The silver halide color photographic light-sensitive material containing the two-equivalent coupler having a group capable of being released upon a coupling reaction represented by the general formula (I) has a high dye forming rate even when it is processed in a color developing solution which does not contain an organic solvent such as benzyl alcohol.

29 Claims, No Drawings

SILVER HALIDE COLOR PHOTOGRAPHIC LIGHT-SENSITIVE MATERIAL COMPRISING COUPLER HAVING NITROGEN-CONTAINING HETEROCYCLIC RING

FIELD OF THE INVENTION

The present invention relates to a photographic coupler. More particularly, it relates to a color photographic light-sensitive material containing a novel two-equivalent photographic coupler.

BACKGROUND OF THE INVENTION

It is known that, by color development of a silver halide color photographic material, the oxidation product of an aromtic primary amine developing agent reacts with a coupler to form a dye such as an indophenol, an indoaniline, an indamine, an azomethine, a phenoxazine, a quinonimine, a phenazine, and the like, thus forming a color image (for example, see T. H. James, *The Theory of the Photographic Process*, 3rd Edition, pages 382 to 396, Macmillan Co., New York (1971)). In this procedure, the subtractive color process is ordinarily used for color reproduction, and silver halide emulsions which are selectively sensitive to blue, green and red light, and yellow, magenta and cyan color image formers, which are respectively the complementary colors of blue, green and red, are employed. For example, a coupler of the acylacetanilide, malondianilide or dibenzoylmethane type is used for forming a yellow color image; coupler of the pyrazolone, pyrazolobenzimidazole, cyanoacetophenone, pyrazolotriazole or indazolone type is generally used for forming a magenta color image; and a phenolic coupler, such as a phenol and a naphthol, is used for forming a cyan color image.

Usually, color photographic light-sensitive materials are roughly divided into two classes, one of which is a coupler-in-developer type color photographic light-sensitive material wherein a coupler is present in the developing solution and the other of which is an incorporated coupler type color photographic light-sensitive material wherein a coupler is incorporated into each light-sensitive layer of the photographic maerial so as to maintain the independent functions thereof. In the latter type of photographic material, a dye image forming coupler is added to a silver halide emulsion layer. The coupler added to an emulsion layer must be rendered non-diffusible (diffusion-resistant) in the binder matrix of the emulsion layer.

On the other hand, a two-equivalent coupler in which a group capable of being released as a result of the coupling reaction with an oxidation product of a developing agent is substituted at the coupling position thereof has been also known. A two-equivalent coupler can form one mole of dye using two moles of silver although at least four moles of silver are required by a four-equivalent coupler in order to form one mole of dye. Therefore, it is possible to reduce the amount of silver coated in the photographic light-sensitive material resulting in a decrease in production cost and a reduction in the film thickness by employing a two-equivalent coupler.

Although known two-equivalent couplers have good characteristics to some extent, improvement in their properties is still desired. In particular, known two-equivalent couplers have insufficient color forming properties which are important in high temperature rapid processing that has recently become populer. In order to compensate for the insufficient color forming properties, an organic solvent such as benzyl alcohol, etc. has been added to a developing solution, if desired. However, organic solvents used to accelerate color formation have several problems. For example, (1) since they are absorbed into emulsion layers during development the amount thereof decreases in the developing solution and thus the color formation becomes poor, (2) they are carried over into a bleaching solution of a bleach-fixing solution and hinder removal of silver or a decrease in dye density results (3) they remain in the photographic material after processing and adversely affect the fastness of dye images, and (4) they are mixed in processing wastes and cause an increase in BOD and COD of the wastes.

For these reasons it has been eagerly desired to eliminate the use organic solvents to accelerate color formation or reduce the amount thereof.

Recently, couplers containing a diffusion-resistant group having a p-hydroxyphenylsulfonyl group or a p-hydroxyphenylsulfinyl group as a terminal group as described in Japanese Patent Application (OPI) No. 42045/83 have been proposed. These couplers are recognized to have improved color forming properties in comparison with conventionally known couplers due to the functions of the diffusion-resistant group. However, the improvement achieved is still not sufficient and they are disadvantageous because they have a low solubility in the organic solvents used for dispersing couplers.

SUMMARY OF THE INVENTION

Therefore, an object of the present invention is to provide a color coupler which has an excellent color forming properties, eliminating the drawbacks present in known couplers, and which is suitable for use in color photographic light-sensitive materials.

Another object of the present invention is to provide a color photographic light-sensitive material having a sufficiently high color forming properties even when it is processed in a color developing solution which does not contain an organic solvent such as benzyl alcohol, etc. to accelerate color formation.

These and other objects of the present invention will become more apparent from the following detailed description and examples.

These objects of the present invention are accomplished by a silver halide color photographic light-sensitive material comprising a support having thereon at least one silver halide emulsion layer, the color photographic light-sensitive material containing a color coupler with a group represented by the general formula (I)

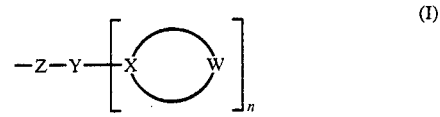

wherein W represents

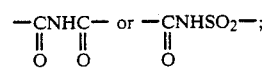

X represents an organic residue necessary for forming a 5-membered or 6-membered nitrogen-containing heterocyclic ring or a condensed ring thereof together with W; Y represents an organic residue connecting Z and X and containing at least one carbon atom which is bonded to Z; Z represents an oxygen atom or a sulfur atom; and n represents an integer of 1 to 2, this group represented by the general formula (I) being present at the coupling position of the color coupler.

DETAILED DESCRIPTION OF THE INVENTION

Of the couplers according to the present invention, preferred couplers are represented by the following general formula (II):

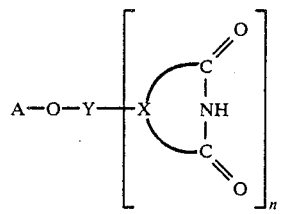

wherein A represents a coupler residue in which one hydrogen atom at the coupling position is eliminated; and X, Y and n each as the same meaning as defined in the general formula (I).

The couplers according to the present invention must be rendered diffusion-resistant since they are employed in an emulsion layer. The diffusion-resistant group is a group which sufficiently increases the molecular weight of the coupler to prevent the coupler from diffusing from the emulsion layer to which the coupler is added. Generally, the diffusion resistant group is an organic group having 10 or more carbon atoms. The effects of the present invention are equivalent where the diffusion-resistant group is present in any of A, Y or X in the general formula (II). It is believed that the effects of the present invention are achieved upon the conversion of —CONHCO— in the cyclic imide group contained in the group capable of being released from the coupler according to the present invention to —CON⊖CO— during development.

In the general formula (II), suitable examples of a yellow color image forming coupler residue represented by A include those of the pivaloyl acetanilide type, the benzoyl acetanilide type, the malonic diester type, the malondiamide type, the dibenzoylmethane type, the benzothiazolyl acetamide type, the malonic ester monoamide type, the benzothiazolyl acetate type, the benzoxazolyl acetamide type, the benzoxazolyl acetate type, the benzimidazolyl acetamide type and the benzimidazolyl acetate type; coupler residues derived from hetero ring-substituted acetamides or hetero ring-substituted acetates as disclosed in U.S. Pat. No. 3,841,880; coupler residues derived from the acylacetamides as described in U.S. Pat. No. 3,770,446, British Pat. No. 1,459,171, West German Patent Application (OLS) No. 2,503,099, Japanese Patent Application (OPI) No. 139738/75 and Research Disclosure, No. 15737; and hetero ring type coupler residues as described in U.S. Pat. No. 4,046,574, etc.

Suitable examples of magenta color image forming coupler residues represented by A include those of the 5-oxo-2-pyrazoline type, the pyrazolobenzimidazole type, the pyrazolotriazole type, the cyanoacetophenone type, the pyrazoloimidazole type and the N-hetero ring-substituted acylacetamide type coupler residues as described in West German Patent Application (OLS) No. 3,121,955, etc.

Suitable examples of cyan color image forming coupler residues represented by A include those with a phenol nucleus or an α-naphthol nucleus.

Suitable examples of substantially non-color forming coupler residues represented by A include those of the indanone type, the acetophenone type, etc., and specific examples thereof are described in U.S. Pat. Nos. 4,052,213, 4,088,491, 3,632,345, 3,958,993, 3,961,959, 4,046,574 and 3,938,996, etc. Such of these compounds compete with dye forming couplers in the reaction with the oxidation product of the developing agent and provide effects of controlling gradation and improving granularity.

Preferred examples of 5-membered or 6-membered nitrogen-containing heterocyclic rings formed with the organic residue represented by X in the general formula (II) include 2,4-dioxoimidazolidine, 2,4-dioxo-1,3-oxazolidine, 3,5-dioxo-1,2,4-triazolidine, phthalimide, succinimide, uracil, glycolimide, xanthene, glutarimide, parabanic acid, 2,6-dioxo-1,2,3,6-tetrahydropyrimidine, urazole, barbituric acid and 2,4-dioxo-1,3-thiazolidine, etc., rings. These heterocyclic rings may be bonded to Y at any position capable of being substituted other than the nitrogen atom in the imide linkage of the heterocyclic ring and may be further substituted. Suitable examples of substituents include an alkyl group, a phenyl group, a halogen atom, an aralkyl group, an alkoxy group, a carboxy group, an acylamino group, an alkoxycarbonyl group, a cyano group, a nitro group, an alkylsulfonamido group, an arylxulfonamido group, a hydroxy group, an alkylthio group, an arylthio group, an imido group, an alkanesulfonyl group, an arylsulfonyl group, a sulfamoyl group which may be substituted with an alkyl group or an aryl group, a sulfamyl group which may be substituted with an alkyl group or an aryl group, a carbamoyl group which may be substituted with an alkyl group or an aryl group, a ureido group which may be substituted with an alkyl group or an aryl group, an amino group which may be substituted with an alkyl group or an aryl group and a urethane group which may be substituted with an alkyl group or an aryl group, etc. The alkyl groups included in these substituents may contain from 1 to 32 carbon atoms and the aryl groups included in these substituents may contain from 6 to 10 carbon atoms. When X contains a diffusion-resistant group, the total number of carbon atoms included therein together with the substituents is preferably at least 10.

The linking group represented by Y in the general formula (II) is a group containing at least one carbon atom through which the group is bonded to the group A—O—. Suitable examples of the linking groups include an aliphatic group (e.g., an alkyl group, an alkenyl group, etc.), an aromatic group (e.g., a phenyl group; a naphthyl group, etc.), etc. Two or more of these linking groups may be bonded through a bonding group described below in an appropriate combination or these linking groups may be bonded to the nitrogen-containing heterocyclic ring or a condensed ring thereof which is formed with X through a bonding group described below.

Examples of bonding groups include an ether bond, a thioether bond, an ester bond, an amido bond, a sulfone bond, a sulfoxide bond, a sulfonamido bond, an azo bond, an imido bond, a ureido bond, an amino bond, a urethane bond, an imino bond, a hydrazo bond and a sulfamido bond, etc. The total member of carbon atoms present in Y is from 1 to 32 and preferably is from 2 to 22. When Y contains a diffusion-resistant group, the total number of carbon atoms present therein together with the substituents is preferably at least 10.

The effects of the present invention are particularly exhibited when A in the general formula (II) represents a coupler residue represented by the general formula (III), (IV), (V), (VI), (VII), (VIII), (IX), (X), (XI), (XII) or (XIII) described below. Couplers with these coupler residues are preferred because of their high coupling rates.

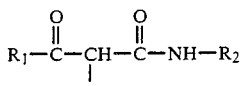 (III)

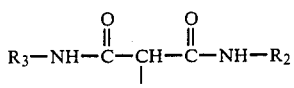 (IV)

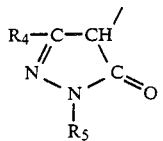 (V)

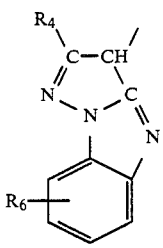 (VI)

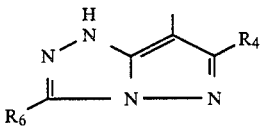 (VII)

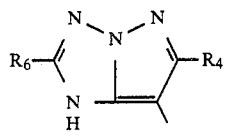 (VIII)

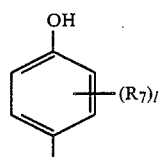 (IX)

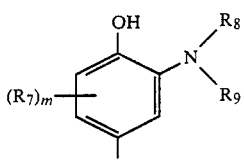 (X)

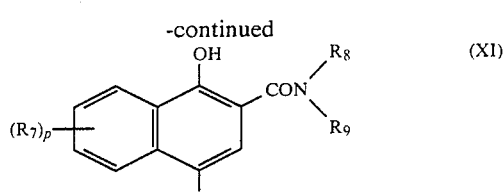 (XI)

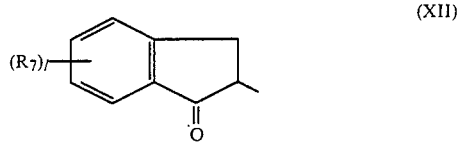 (XII)

$R_{10}-CH-R_{11}$ (XIII)

In the above-described formulae, the free bond attached to the coupling position indicates the position to which the group capable of being released upon coupling is bonded. When $R_1$, $R_2$, $R_3$, $R_4$, $R_5$, $R_6$, $R_7$, $R_8$, $R_9$, $R_{10}$ or $R_{11}$ in the above-described formulae contains a diffusion-resistant group, it is to selected that the total number of carbon atoms present therein is from 8 to 32 and preferably from 10 to 22. On the other hand, when $R_1$, $R_2$, $R_3$, $R_4$, $R_5$, $R_6$, $R_7$, $R_8$, $R_9$, $R_{10}$ or $R_{11}$ does not contain a diffusion-resistant group, the total number of carbon atoms present therein is preferably not more than 15.

$R_1$ to $R_{11}$, l, m and p in the above-described general formulae (III) to (XIII) are explained below.

In the above-described formulae, $R_1$ represents an aliphatic group, an aromatic group, an alkoxy group or a heterocyclic group; and $R_2$ and $R_3$ each represents an aromatic group or a heterocyclic group.

The aliphatic groups represented by $R_1$ is preferably an aliphatic group containing from 1 to 22 carbon atoms, and may be unsubstituted or substituted, and further, may have a chain form or a cyclic form. Preferred substituents for the aliphatic group for $R_1$ include an alkoxy group, an aryloxy group, an amino group, an acylamino group, a halogen atom, etc., each of which may further be substituted. Specific examples of aliphatic groups useful for $R_1$ include an isopropyl group, an iso-butyl group, a tert-butyl group, an iso-amyl group, a tert-amyl group, a 1,1-dimethylbutyl group, a 1,1-dimethylhexyl group, a 1,1-diethylhexyl group, a dodecyl group, a hexadecyl group, an octadecyl group, a cyclohexyl group, a 2-methoxyisopropyl group, a 2-phenoxyisopropyl group, a 2-tertbutylphenoxyisopropyl group, an α-aminoisopropyl group, an α-(diethylamino)isopropyl group, an α-(succinimido)isopropyl group, an α-(phthalimido)isopropyl group, an α-(benzenesulfonamido)isopropyl group, etc.

While $R_1$, $R_2$ or $R_3$ represents an aromatic group (especially a phenyl group), the group may contain a substituent. An aromatic group as a phenyl group, etc. may be substituted with an alkyl group, an alkenyl group, an alkoxy group, an alkoxycarbonyl group, an alkoxycarbonylamino group, an aliphatic amido group, an alkylsulfamoyl group, an alkylsulfonamido group, an alkylureido, alkyl-substituted succinimido group, etc. each containing 32 or less carbon atoms. The alkyl group therein may be an alkyl group which contains an aromatic group such as phenylene in its main chain. Further, the phenyl group represented by $R_1$, $R_2$ or $R_3$ may be substituted with an aryloxy group, an aryloxycarbonyl group, an arylcarbamoyl group, an arylamido group, an arylsulfamoyl group, an arylsulfonamido group, an arylureido group, etc., the aryl moiety of which groups each may be substituted with one or more alkyl groups wherein the total number of carbon atoms is from 1 to 22.

Furthermore, the phenyl group represented by $R_1$, $R_2$ or $R_3$ may be substituted with an amino group which includes an amino group substituted with a lower alkyl group having from 1 to 6 carbon atoms, a hydroxy group, a carboxy group, a sulfo group, a nitro group, a cyano group, a thiocyano group or a halogen atom.

In addition, $R_1$, $R_2$ or $R_3$ may represent a substituent formed by condensing a phenyl group and another ring, such as a naphthyl group, a quinolyl group, an isoquinolyl group, a chromanyl group, a coumaranyl group, a tetrahydronaphthyl group, etc. These groups may further have substituents in themselves.

Where $R_1$ represents an alkoxy group, the alkyl moiety thereof can be a straight chain or branched chain alkyl group having from 1 to 32 carbon atoms, preferably from 1 to 22 carbon atoms, an alkenyl group, a cyclic alkyl group or a cyclic alkenyl group, each of which may be substituted with a halogen atom, an aryl group, an alkoxy group, etc.

Where $R_1$, $R_2$ or $R_3$ represents a heterocyclic group, the heterocyclic group is bonded to the carbon atom of the carbonyl group of the acyl moiety or the nitrogen atom of the amido moiety of an α-acylacetamido group through one of the carbon atoms forming the ring. Examples of such heterocyclic rings include thiophene, furan, pyran, pyrrole, pyrazole, pyridine, pyrazine, pyrimidine, pyridazine, indolizine, imidazole, thiazole, oxazole, triazine, thiadiazine, oxazine, etc. These rings may further be substituted.

$R_5$ in the general formula (V) represents a straight chain or branched chain alkyl group having from 1 to 32 carbon atoms, preferably from 1 to 22 carbon atoms (e.g., a methyl group, an isopropyl group, a tert-butyl group, a hexyl group, a dodecyl group, etc.), an alkenyl group (e.g., an allyl group, etc.), a cyclic alkyl group (e.g., a cyclopentyl group, a cyclohexyl group, a norbornyl group, etc.), an aralkyl group (e.g., a benzyl group, a β-phenylethyl group, etc.), a cyclic alkenyl group (e.g., a cyclopentenyl group, a cyclohexenyl group, etc.), etc., which groups each may be substituted with a halogen atom, a nitro group, a cyano group, an aryl group, an alkoxy group, an aryloxy group, a carboxy group, an alkylthiocarbonyl group, an arylthiocarbonyl group, an alkoxycarbonyl group, an aryloxycarbonyl group, a sulfo group, a sulfamoyl group, a carbamoyl group, an acylamino group, a diacylamino group, a ureido group, a urethane group, a thiourethane group, a sulfonamido group, a heterocyclic group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxy group, a mercapto group, etc.

$R_5$ in the general formula (V) may further represent an aryl group (e.g., a phenyl group, an α- or β-naphthyl group, etc.). The aryl group may also be substituted with one or more substituents. Specific examples of substituents which can be present include an alkyl group, an alkenyl group, a cyclic alkyl group, an aralkyl group, a cyclic alkenyl group, a halogen atom, a nitro group, a cyano group, an aryl group, an alkoxy group, an aryloxy group, a carboxy group, an alkoxycarbonyl group, an aryloxycarbonyl group, a sulfo group, a sulfamoyl group, a carbamoyl group, an acylamino group, a diacylamino group, a ureido group, a urethane group, a sulfonamido group, a heterocyclic group, an arylsulfonyl group, an alkylsulfonyl group, an arylthio group, an alkylthio group, an alkylamino group, a dialkylamino group, an anilino group, an N-alkylanilino group, an N-arylanilino group, an N-acylanilino group, a hydroxy group, a mercapto group, etc. An especially preferable substituent for $R_5$ is a phenyl group which is substituted with an alkyl group, an alkoxy group, a halogen atom, etc., at at least one of the o-positions, because coloration of couplers remaining in film layers due to light or heat is effectively restrained.

Furthermore, $R_5$ may represent a heterocyclic group (e.g., a 5-membered or 6-membered heterocyclic ring containing, as a hetero atom, a nitrogen atom, an oxygen atom or a sulfur atom, or a condensed ring thereof. Specific examples include a pyridyl group, a quinolyl group, a furyl group, a benzothiazolyl group, an oxazolyl group, an imidazolyl group, a naphthoxazolyl group, etc.), a heterocyclic group substituted with one or more substituents as defined for the above-described aryl group, an aliphatic acyl group, an aromatic acyl group, an alkylsulfonyl group, an arylsulfonyl group, an alkylcarbamoyl group, an arylcarbamoyl group, an alkylthiocarbamoyl group or an arylthiocarbamoyl group.

$R_4$ in the general formula (V), (VI), (VII) or (VIII) represents a hydrogen atom, a straight chain or branched chain alkyl group having from 1 to 32 carbon atoms, preferably from 1 to 22 carbon atoms, an alkenyl group, a cyclic alkyl group, an aralkyl group or a cyclic alkenyl group (each of which may have one or more substituents as defined for the above-described substituents $R_5$), an aryl group or a heterocyclic group (each of which also may have one or more substituents as defined for the above-described substituent $R_5$), an alkoxycarbonyl group (e.g., a methoxycarbonyl group, an ethoxycarbonyl group, a stearyloxycarbonyl group, etc.), an aryloxycarbonyl group (e.g., a phenoxycarbonyl group, a naphthoxycarbonyl group, etc.), an aralkyloxycarbonyl group (e.g., a benzyloxycarbonyl group, etc.), an alkoxy group (e.g., a methoxy group, an ethoxy group, a heptadecyloxy group, etc.), an aryloxy group (e.g., a phenoxy group, a tolyloxy group, etc.), an alkylthio group (e.g., an ethylthio group, a dodecylthio group, etc.), an arylthio group (e.g., a phenylthio group, an α-naphthylthio group, etc.), a carboxy group, an acylamino group (e.g., an acetylamino group, a 3-[(2,4-di-tert-amylphenoxy)acetamido]benzamido group, etc.), a diacylamino group, an N-alkylacylamino group (e.g., an N-methylpropionamido group, etc.), an N-arylacylamino group (e.g., an N-phenylacetamido group, etc.), a ureido group (e.g., a ureido group, an N-arylureido group, an N-alkylureido group, etc.), a urethane group, a thiourethane group, an arylamino group (e.g., a phenylamino group, an N-metylaninino group, a diphenylamino group, an N-acetylanilino group, a 2-chloro-5-tetradecanamido anilino group, etc.), an alkylamino group (e.g., a n-butylamino group, a methylamino group, a cyclohexylamino group, etc.), a cycloamino group (e.g., a piperidino group, a pyrrolidino group, etc.), a heterocyclic amino group (e.g., a 4-pyridylamino group, a 2-benzoxazolylamino group, etc.), an alkylcarbonyl group (e.g., an acetyl group, etc.), an arylcarbonyl group (e.g., a benzoyl group, etc.), a sulfonamido group (e.g., an alkylsulfonamido group, an arylsulfonamido group, etc.), a carbamoyl group (e.g., an ethylcarbamoyl group, a dimethylcarbamoyl group, an N-methylphenylcarbamoyl group, an N-phenylcarbamoyl, etc.), a sulfamoyl group (e.g., an N-alkylsulfamoyl group, an N,N-dialkylsulfamoyl group, an N-arylsulfamoyl group, an N-alkyl-N-arylsulfamoyl group, an N,N-diarylsulfamoyl group, etc.), a cyano group, a hydroxy group, a mercapto group, a halogen atom or a sulfo group.

$R_6$ in the general formula (VI), (VII) or (VIII) represents a hydrogen atom, or a straight chain or branched chain alkyl group having from 1 to 32 carbon atoms, preferably from 1 to 22 carbon atoms, an alkenyl group, a cyclic alkyl group, an aralkyl group or a cyclic alkenyl group, each of which may have one or more substituents as defined for the above-described substituent $R_5$.

Further, $R_6$ may represent an aryl group or a heterocyclic group, each of which may have one or more substituents as defined for the above-described substituent $R_5$.

Furthermore, $R_6$ may represent a cyano group, an alkoxy group, an aryloxy group, a halogen atom, a carboxy group, an alkoxycarbonyl group, an aryloxycarbonyl group, an acyloxy group, a sulfo group, a sulfamoyl group, a carbamoyl group, an acylamino group, a diacylamino group, a ureido group, a urethane group, a sulfonamido group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxy group or a mercapto group.

$R_7$, $R_8$ and $R_9$ in the general formula (IX), (X), (XI) or (XII) represent groups which have been employed in conventional 4-equivalent type pheno or α-naphthol couplers. Specifically, $R_7$ represents a hydrogen atom, a halogen atom, an alkoxycarbonylamino group, an aliphatic hydrocarbon residue, an N-arylureido group, an acylamino group, an —O—$R_{12}$ group or an —S—$R_{12}$ group (wherein $R_{12}$ is an aliphatic hydrocarbon residue). When two or more $R_7$ groups are present in one molecule, they may be the same or different. The above-described aliphatic hydrocarbon residues may also be substituted. Suitable substituents include an aryl group, where the aryl group may also have one or more substituents as defined for the above-described substituent $R_5$.

$R_8$ and $R_9$ each represents an aliphatic hydrocarbon residue, an aryl group or a heterocyclic group. Either of $R_8$ and $R_9$ may be a hydrogen atom. The above-described groups for $R_8$ and $R_9$ may also be substituted. Furthermore, $R_8$ and $R_9$ may combine and form a nitrogen-containing heterocyclic nucleus. More specifically, the above-described aliphatic hydrocarbon residue includes both saturated and unsaturated residues each of which may be straight chain, branched chain or cyclic. Preferred examples thereof include an alkyl group (e.g., a methyl group, an ethyl group, a propyl group, an isopropyl group, a butyl group, a t-butyl group, an isobutyl group, a dodecyl group, an octadecyl group, a cyclobutyl group, a cyclohexyl group, etc.) and an alkenyl group (e.g., an allyl group, an octenyl group, etc.). Examples of the above-described aryl group include a phenyl group, a naphthyl group, etc. Representative examples of the above-described heterocyclic group include a pyridinyl group, a quinolyl group, a thienyl group, a piperidyl group, an imidazolyl group, etc. These aliphatic hydrocarbon residues, aryl groups and heterocyclic groups each may be substituted with a halogen atom, a nitro group, a hydroxy group, a carboxy group, an amino group, a substituted amino group, a sulfo group, an alkyl group, an alkenyl group, an aryl group, a heterocyclic group, an alkoxy group, an aryloxy group, an arylthio group, an arylazo group, an acylamino group, a carbamoyl group, an ester group, an acyl group, an acyloxy group, a sulfonamido group, a sulfamoyl group, a sulfonyl group, a morpholino group, etc.

In the above-described general formulae, l represents an integer of 1 to 4, m represents an integer of 1 to 3, and p represents an integer of 1 to 5.

$R_{10}$ in the general formula (XIII) represents an arylcarbonyl group, an alkanoyl group having from 2 to 32 carbon atoms, preferably from 2 to 22 carbon atoms, an arylcarbamoyl group, an alkylcarbamoyl group having from 2 to 32 carbon atoms, preferably from 2 to 22 carbon atoms, an alkoxycarbonyl group having from 1 to 32 carbon atoms, preferably from 1 to 22 carbon atoms or an aryloxycarbonyl group, each of which may be substituted. Examples of suitable substituents include an alkoxy group, an alkoxycarbonyl group, an acylamino group, an alkylsulfamoyl group, an alkylsulfonamido group, an alkylsuccinimido group, a halogen atom, a nitro group, a carboxy group, a nitrile group, an alkyl group, an aryl group, etc.

$R_{11}$ in the general formula (XIII) represents an arylcarbonyl group, an alkanoyl group having from 2 to 32 carbon atoms, preferably from 2 to 22 carbon atoms, an arylcarbamoyl group, an alkylcarbamoyl group having from 2 to 32 carbon atoms, preferably from 2 to 22 carbon atoms, an alkoxycarbonyl group having from 1 to 32 carbon atoms, preferably from 1 to 22 carbon atoms, an aryloxycarbonyl group, an alkylsulfonyl group having from 1 to 32 carbon atoms, preferably from 1 to 22 carbon atoms, an arylsulfonyl group, an aryl group or a 5-membered or 6-membered heterocyclic group (containing as a hetero atom a nitrogen atom, an oxygen atom or a sulfur atom, with specific examples including a triazolyl group, an imidazolyl group, a phthalimido group, a succinimido group, a furyl group, a pyridyl group, a benzotriazolyl group, etc.), each of which may have one or more substituents as defined for the above-described substituent $R_{10}$.

In the general formula (II), a particularly preferred coupler residue represented by A is a coupler residue represented by the general formula (III) wherein $R_1$ represents a tert-butyl group and $R_2$ represents an aromatic group.

In the general formula (II), the linking group represented by Y preferably contains a phenylene group, the carbon atoms of which is bonded to the oxygen atom which is in turn attached to the coupling position of the coupler. Where Y may also contain an aliphatic residue, an aromatic residue, an ether bond, an ester bond, a sulfone bond, a sulfonamido bond, an amido bond, a sulfamido bond or a ureido bond in the bonding connected to X.

Specific examples of couplers which can be effectively used in the present invention are illustrated below, but the present invention should not be construed as being limited thereto.

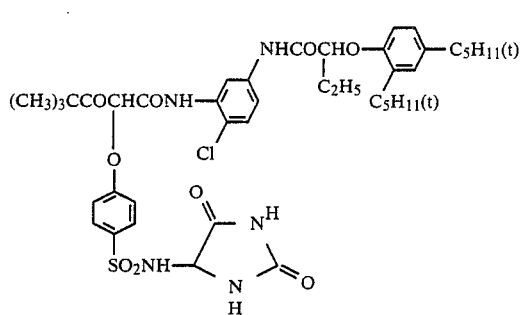
(1)
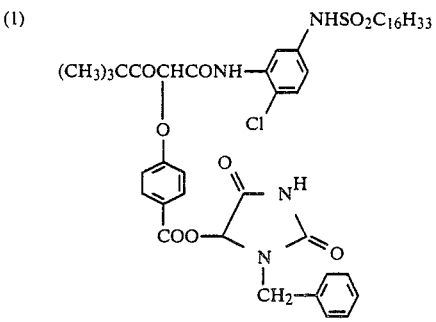
(2)
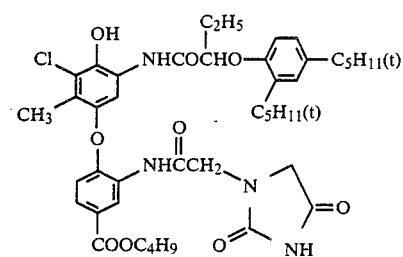
(3)
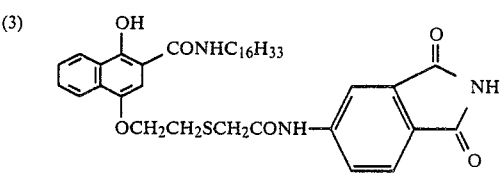
(4)
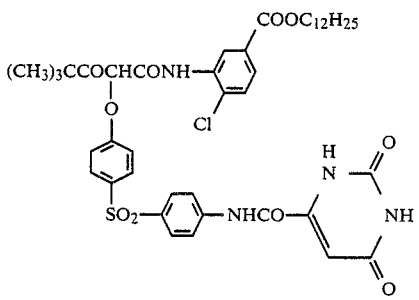
(5)
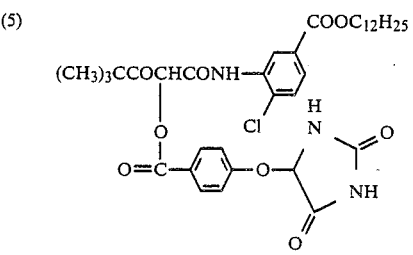
(6)
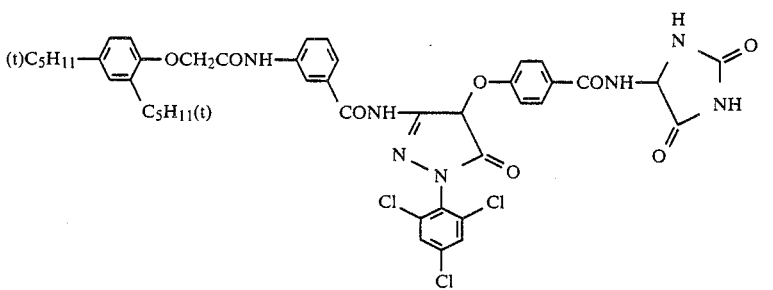
(7)
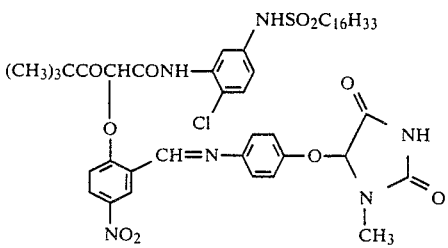
(8)

(9)
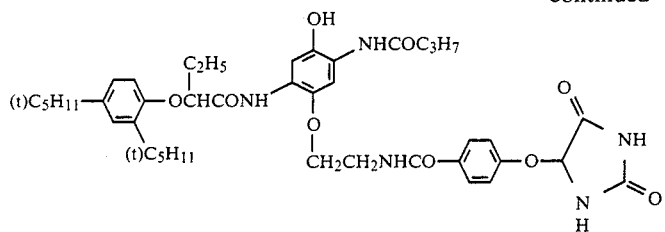
(10)
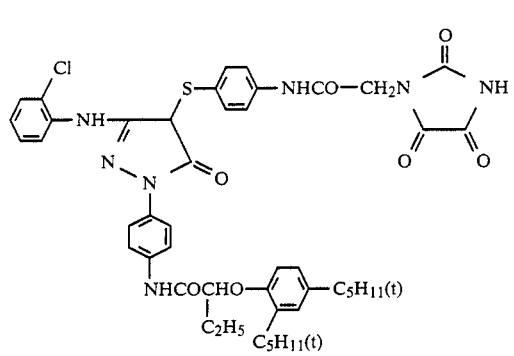
(11)
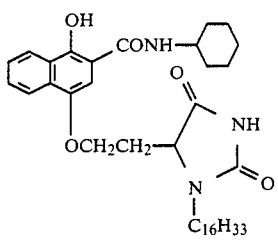
(12)
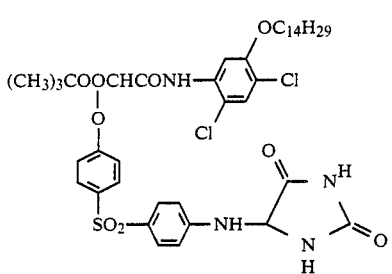
(13)
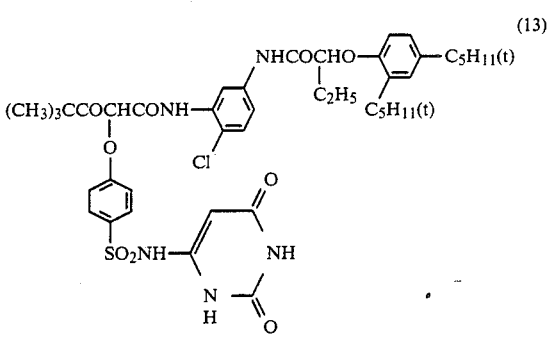
(14)
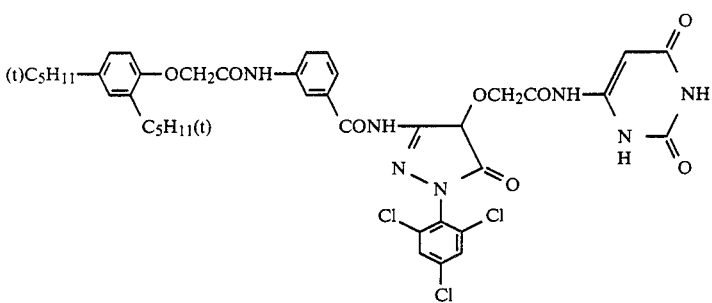
(15)
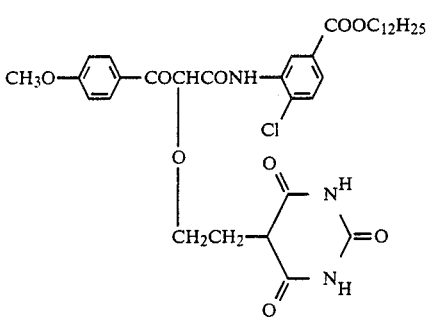
(16)
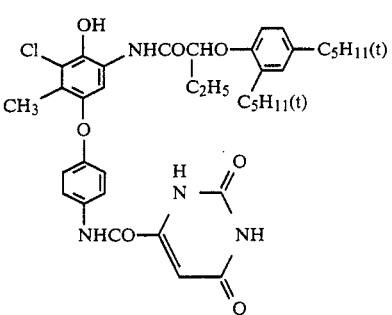

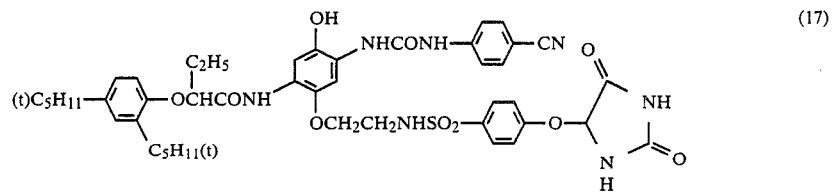
(17)
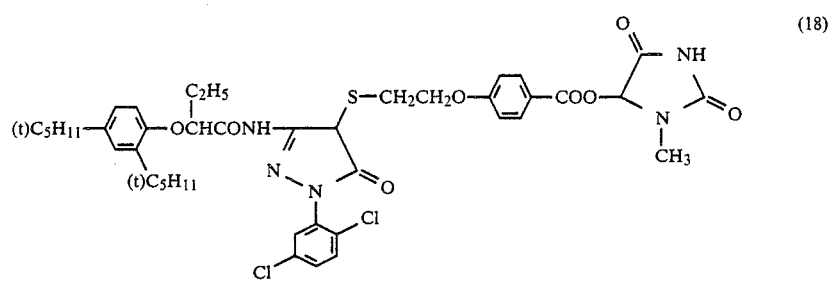
(18)
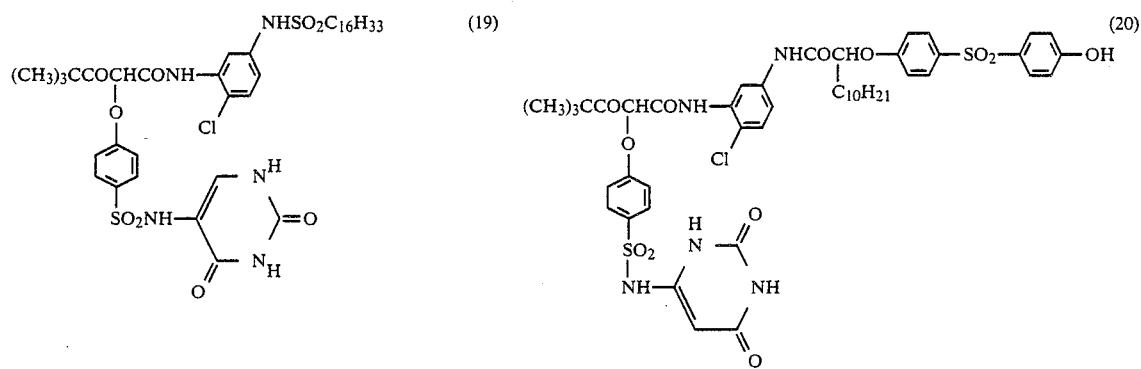
(19) (20)
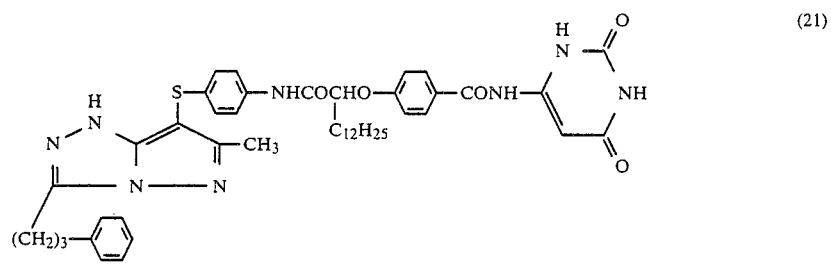
(21)
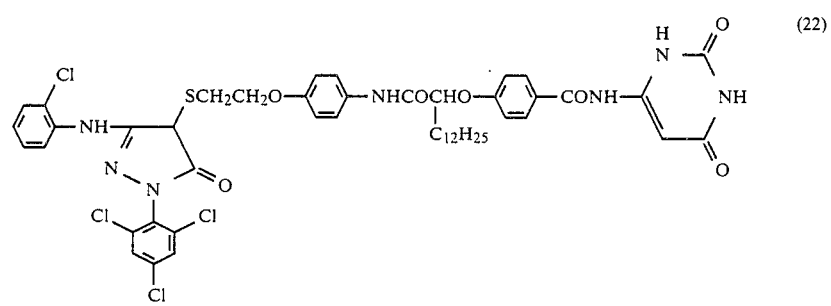
(22)

-continued
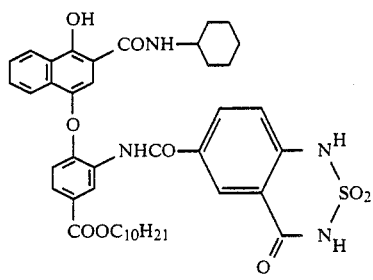 (23)
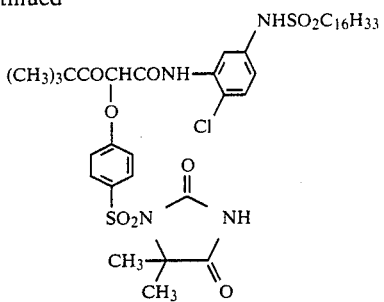 (24)
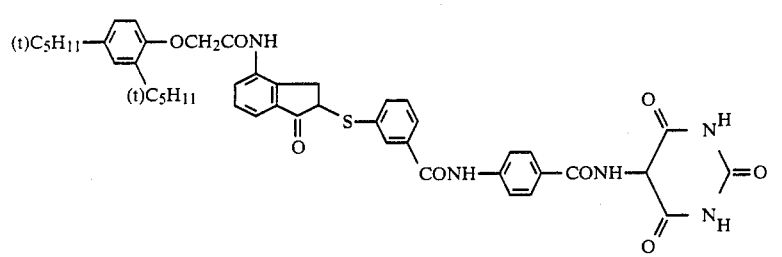 (25)
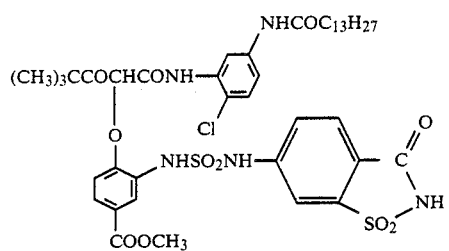 (26)
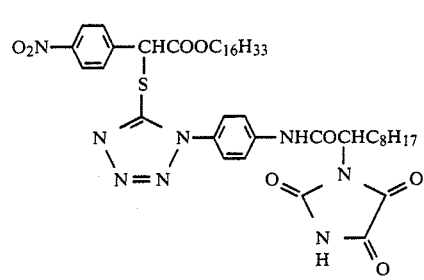 (27)
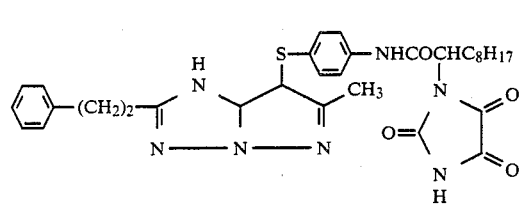 (28)
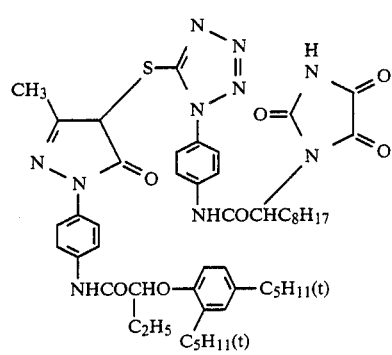 (29)
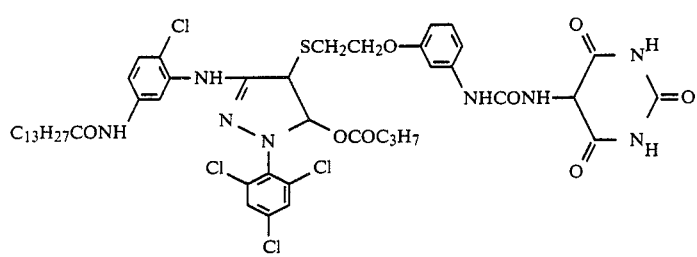 (30)

(31)

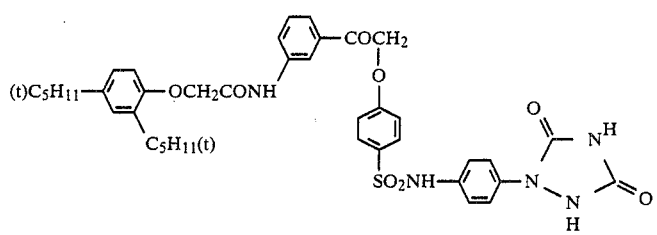

(32)

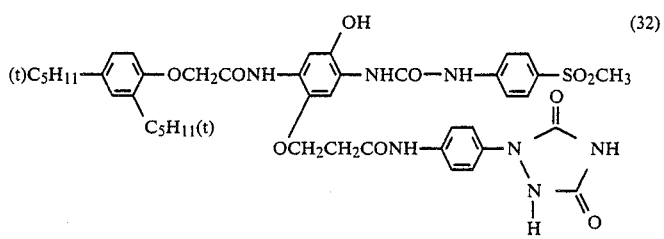

(33)

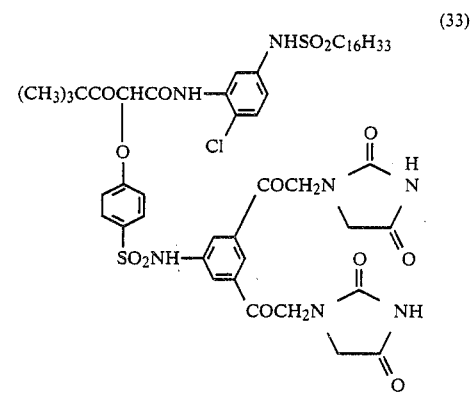

The couplers according to the present invention can be synthesized using a combination of known methods. An acylacetamide type coupler having an aryloxy group as a group capable of being released on coupling can be synthesized by halogenating the coupling position of a four-equivalent coupler and reacting the product obtained with a phenol compound in the presence of a base. Ether releasing type coupler, i.e., 5-pyrazolone type couplers, phenol type couplers, naphthol type couplers and certain acylacetamide type couplers, each having an oxygen atom and capable of releasing the ether moiety, can be synthesized by reacting a compound prepared by introducing a hydroxy group at the coupling position of a four-equivalent coupler with an active halogenated compound in the presence of a base. A thioether releasing type coupler can be generally synthesized by reacting a four-equivalent coupler with a sulfenyl chloride to form a group capable of being released in the presence of or in the absence of a base. These methods of synthesizing two-equivalent couplers are described in the known literature, for example, U.S. Pat. Nos. 3,894,875, 3,933,501, 4,296,199, 3,227,554, 3,476,563, 4,296,200, 4,234,678, 4,228,233, 4,351,897, 4,264,723, 4,366,237 and 3,408,194, Japanese Patent Application (OPI) Nos. 70871/82, 96343/82 and 52423/78, etc.

In synthesizing the couplers according to the present invention, a method in which a group capable of being released is introduced after formation of a coupler skeleton is generally employed advantageously. However, a method can be used in which at first a two-equivalent coupling group of a coupler is prepared, an active functional group such as an amino group, etc. is formed by reduction or other appropriate procedures and then a diffusion-resistant group is introduced thereinto. Introduction of a cyclic imido group which forms a partial structure of a group capable of being released upon coupling into a coupler can be carried out at the last step in the synthesis or a cyclic imido group can be introduced into a group capable of being released upon coupling before introduction of the latter group into a 4-equivalent coupler. The synthesis route can be appropriately selected depending on the structure of the desired coupler.

Typical examples of synthesizing couplers according to the present invention are specifically set forth below. Unless otherwise indicated, all parts, percents, ratios and the like are by weight.

SYNTHESIS EXAMPLE 1

Synthesis of Coupler (1)

A mixture of 19.5 g of α-bromo-α-pivaloyl-2-chloro-5-[1-(2,4-di-tert-amylphenoxy)butyramido]acetanilide, 21.3 g of 5-(4-hydroxybenzenesulfonamido)-3-pivaloyl-2,4-dioxoimidazolidine, 6.4 g of potassium tert-butoxide and 200 ml of acetonitrile was reacted at room temperature for 5 hours. The reaction mixture was poured into 500 ml of water and extracted with 200 ml of ethyl acetate. The oil layer was washed with water, then washed with 500 ml of a 1N aqueous solution of hydrochloric acid and further repeatedly washed with water until the washing water became neutral. The oil layer was separated and concentrated under reduced pressure. The residue was dissolved in 200 ml of tetrahydrofuran, to which was added a solution containing 6 g of potassium hydroxide dissolved in 20 ml of methanol and the mixture was allowed to stand at room temperature (about 20°–30° C.) overnight. 200 ml of ethyl acetate was then added and the mixture was washed with 1 liter of water. After washing with a 1N aqueous solution of hydrochloric acid, the mixture was washed with water and the oil layer was separated. The oil layer was dried over anhydrous sodium sulfate, the solvent was distilled off under reduced pressure and to the residue was added diethyl ether to crystallize. 11 g of the desired Coupler (1) was obtained.

SYNTHESIS EXAMPLE 2

Synthesis of Coupler (3)

To a mixture of 20 g of 4-(2-amino-4-butoxycarbonylphenoxy)-2-[2-(2,4-di-tert-amylphenoxy)butyramido]-6-chloro-5-methylphenol (synthesized by the method as described in U.S. Pat. No. 4,004,929), 5.2 g of 2,4-dioxoimidazolidin-1-yl acetate and 100 ml of N,N-dimethylformamide was added dropwise a solution containing 6.2 g of N,N'-dicyclohexylcarbodiimide dissolved in 10 ml of ethyl acetate at room temperature. After stirring the mixture for 4 hours, the N,N'-dicyclohexylurea thus-deposited was removed by filtration. The reaction mixture was poured into 1 liter of water and extracted with 500 ml of ethyl acetate. After washing with water, the oil layer was separated and the solvent was distilled off under reduced pressure. To the residue was added diethyl ether to crystallize and 19 g of the desired Coupler (3) was obtained.

SYNTHESIS EXAMPLE 3

Synthesis of Coupler (4)

To a mixture of 16.4 g of 2-(3-hexadecylcarbamoyl-4-hydroxynaphthoxy)ethylthioacetic acid, 5 g of 4-aminophthalimide and 100 L ml of N,N-dimethylformamide was added dropwise a solution containing 6.2 g of N,N'-dicyclohexylcarbodiimide dissolved in 20 ml of ethyl acetate at room temperature. After stirring the mixture for 4 hours, the N,N'-dicyclohexylurea thus-deposited was removed by filtration. The reaction mixture was poured into 1 liter of water and extracted with 500 ml of ethyl acetate. After washing with water, the oil layer was separated and the solvent was distilled off under reduced pressure. To the residue was added diethyl ether to crystallize and 12 g of the desired Coupler (4) was obtained.

The amount of couplers to be used and components other than the coupler according to the present invention in the color photographic light-sensitive material of the present invention are described below.

The amount of the coupler according to the present invention and other couplers used is not particularly restricted and the amount of the coupler is preferably from $2 \times 10^{-3}$ mol to $5 \times 10^{-1}$ mol, particularly from $1 \times 10^{-2}$ mol to $5 \times 10^{-1}$ mol, per mol of silver in the silver halide emulsion layer.

Conventional methods, e.g., the method described in U.S. Pat. No. 2,322,027, can be employed to incorporate the coupler into the silver halide emulsion layer. For example, the coupler can be dissolved either in an organic solvent having a high boiling point such as phthalic acid alkyl esters (e.g., dibutyl phthalate, dioctyl phthalate, etc.), phosphoric acid esters (e.g., diphenyl phosphate, triphenyl phosphate, tricresyl phosphate, dioctylbutyl phosphate, etc.), citric acid esters (e.g., tributyl acetylcitrate, etc.), benzoic acid esters (e.g., octyl benzoate, etc.), alkyl amides (e.g., diethyl laurylamide, etc.), fatty acid esters (e.g., dibutoxyethyl succinate, etc.), trimesic acid esters, etc.; or an organic solvent having a low boiling point of from about 30° to 150° C. such as a lower alkyl acetate (e.g., ethyl acetate, butyl acetate, etc.), ethyl propionate, sec-butyl alcohol, methyl iso-butyl ketone, β-ethoxyethyl acetate, methyl cellosolve acetate, etc. Then, the solution is dispersed in a hydrophilic colloid. The above-described organic solvents having a high boiling point and the above-described organic solvents having a low boiling point may be used alone or as mixtures, if desired.

Known open chain ketomethylene type couplers can be used as yellow color forming couplers. Of these couplers, benzoyl acetanilide type and pivaloyl acetanilide type compounds are advantageous. Specific examples of yellow color forming couplers which can be employed are described, for example, in U.S. Pat. Nos. 2,875,057, 3,265,506, 3,408,194, 3,551,155, 3,582,322, 3,725,072, 4,356,258 and 3,891,445, West German Pat. No. 1,547,868, West German Patent Application (OLS) Nos. 2,219,917, 2,261,361 and 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76, 87650/75, 82424/77 and 115219/77, etc.

Pyrazolone type compounds, indazolone type compounds, cyanoacetyl type compounds, etc. can be used as magenta color forming couplers, and pyrazolone type compounds are particularly advantageous. Specific examples of magenta color forming couplers which can be employed are those described, for example, in U.S. Pat. Nos. 2,600,788, 2,983,608, 3,062,653, 3,127,269, 3,311,476, 3,419,391, 3,519,429, 3,558,319, 3,582,322, 3,615,506, 3,834,908, 3,891,445, 4,367,282, 4,366,237, 4,351,897, 7,388,393 and 4,241,168, West German Pat. No. 1,810,464, West German Patent Application (OLS) Nos. 2,408,665, 2,417,945, 2,418,959 and 2,424,467, Japanese Patent Publication No. 6031/65, Japanese Patent Application (OPI) Nos. 20826/76, 58922/77, 129538/74, 74027/74, 159336/75, 42121/77, 74028/74, 60233/75, 26541/76 and 55122/78, etc.

Phenol type compounds, naphthol type compounds, etc., can be employed as cyan color forming couplers. Specific examples of cyan color forming couplers which can be employed are those described, for example, in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411, 4,004,929, 4,362,810, 4,368,257, 4,341,864, 4,333,999, 4,342,825 and 4,345,025, West German Patent Application (OLS) Nos. 2,414,830 and 2,454,329, Japanese Patent Application (OPI) Nos. 59838/73, 26034/76, 5055/73, 146828/76, 69624/77 and 90932/77, etc.

Colored couplers which can be employed are described, for example, in U.S. Pat. Nos. 3,476,560, 2,521,908 and 3,034,892, Japanese Patent Publication Nos. 2016/69, 22335/63, 11304/67 and 32461/69, Japanese Patent Application (OPI) Nos. 26034/76 and 42121/77, West German Patent Application (OLS) No. 2,418,959, etc.

Development inhibitor releasing (DIR) couplers which can be employed are described, for example, in U.S. Pat. Nos. 3,227,554, 3,617,291, 3,701,783, 3,790,384, 3,632,345, 4,355,100 and 4,248,962, West German Patent Application (OLS) Nos. 2,414,006, 2,454,301, 2,454,329, and 3,209,486, British Pat. No. 953,454, Japanese Patent Application (OPI) Nos. 69624/77, 122335/74, Japanese Patent Publication No. 16141/76, etc.

In addition to DIR couplers, other compounds which release development inhibitors upon development can also be present in the photographic light-sensitive material. For example, the DIR compounds as described, for example, in U.S. Pat. Nos. 3,297,445 and 3,379,529, West German Patent Application (OLS) No. 2,417,914, Japanese Patent Application (OPI) Nos. 15271/77 and 9116/78, etc., can be employed.

Two or more kinds of the couplers described above can be present in the same layer or the same coupler compound can also be present in two or more layers. These couplers are present in the emulsion layer, generally in an amount of from $2 \times 10^{-3}$ mol to $5 \times 10^{-1}$ mol, preferably $1 \times 10^{-2}$ mol to $5 \times 10^{-1}$ mol, per mol of silver.

The hydrophilic colloid layers of the photographic light-sensitive materials prepared in accordance with the present invention can contain ultraviolet light absorbing agents. For example, benzotriazole compounds substituted with an aryl group (e.g., those described in U.S. Pat. No. 3,533,794), 4-thiazolidone compounds (e.g., those described in U.S. Pat. Nos. 3,314,794 and 3,352,681), benzophenone compounds (e.g., those described in Japanese Patent Application (OPI) No. 2784/71), cinnamic acid ester compounds (e.g., those described in U.S. Pat. Nos. 3,705,805 and 3,707,375), butadiene compounds (e.g., those described in U.S. Pat. No. 4,045,229) or benzoxazole compounds (e.g., those described in U.S. Pat. No. 3,700,455) can be employed. Furthermore, the compounds as described in U.S. Pat. No. 3,499,762, Japanese Patent Application (OPI) No. 48535/79 can also be used. Ultraviolet light absorbing couplers (e.g., α-naphthol type cyan dye forming couplers) and ultraviolet light absorbing polymers can also be employed. These ultraviolet light absorbing agents can be mordanted in a specific layer(s), if desired.

The photographic emulsion used in the present invention can be prepared using the methods described in, e.g., P. Glafkides, *Chimie et Physique Photographique*, Paul Montel (1967), G. F. Duffin, *Photographic Emulsion Chemistry*, The Focal Press (1966), V. L. Zelikman, et al., *Making and Coating Photographic Emulsions*, The Focal Press (1964), etc. That is, any of the acid method, the neutral method, the ammonia method and other methods can be used. Moreover, a soluble silver salt can be reacted with a soluble halogen salt using any of the single jet method, the double jet method and a combination thereof.

A method in which grains are formed in the presence of an excess of silver ions (i.e., the so-called reverse mixing method) can also be used. As one of the modes of the double jet method, the method in which the pAg of the liquid phase in which the silver halide is to be produced is kept constant, that is, the so-called controlled double jet method, can be used. This method can provide silver halide emulsions having a regular crystal form and a substantially uniform grain size.

Two or more silver halide emulsions which are seprately prepared can be mixed and then used, if desired.

In the process of the formation of the silver halide grains or physical ripening, cadmium salts, zinc salts, lead salts, thallium salts, iridium salts or complex salts thereof, rhodium salts or complex salts thereof, iron salts or iron complex salts, etc. can be present.

Gelatin can advantageously be used as the binder or protective colloid for the photographic emulsion used in the present invention. However, other hydrophilic colloids can be used as well. For example, proteins such as gelatin derivatives, graft polymers between gelatin and other polymers, albumin, casein, etc.; cellulose derivatives such as hydroxyethyl cellulose, carboxymethyl cellulose, cellulose sulfates, etc.; saccharide derivatives such as sodium alginate, starch derivatives, etc.; and various synthetic hydrophilic polymers of homo- or copolymers such as polyvinyl alcohol, polyvinyl alcohol partial acetal, poly-N-vinylpyrrolidone, polyacrylic acid, polymethacrylic acid, polyacrylamide, polyvinylimidazole, polyvinylpyrazole, etc., can be used as the binder or protective colloid for the photographic emulsion.

Acid-processed gelatin and enzyme-processed gelatin as described in *Bull. Soc. Sci. Photo. Japan*, No. 16, p. 30 (1966) can be used as well as lime-processed gelatin as the gelatin component. In addition, the hydrolyzed products of gelatin and enzyme-decomposition products of gelatin are also suitable. Suitable gelatin derivatives which can be used include those obtained by reacting gelatin with various compounds, such as acid halides, acid anhydrides, isocyanates, bromoacetic acid, alkanesultones, vinylsulfonamides, maleinimide compounds, polyalkylene oxides, epoxy compounds, etc. Specific examples thereof are described in U.S. Pat. Nos. 2,614,928, 3,132,945, 3,186,846 and 3,312,553, British Pat. Nos. 861,414, 1,033,189 and 1,005,784, Japanese Patent Publication No. 26845/67, etc.

Examples of the above-described gelatin graft polymers include those which are obtained by grafting homo- or copolymers of vinyl monomers such as acrylic acid, methacrylic acid, the ester or amide derivatives thereof, acrylonitrile, styrene, etc. to gelatin. In particular, graft polymers with a polymer having some compatibility with gelatin, such as polymers of acrylic acid, methacrylic acid, acrylamide, methacrylamide, hydroxyalkyl methacrylates, etc., are preferred. Examples thereof are described in U.S. Pat. Nos. 2,763,625, 2,831,767 and 2,956,884, etc. Typical synthetic hydrophilic polymer materials are described in, e.g., West German Patent Application (OLS) No. 2,312,708, U.S. Pat. Nos. 3,620,751 and 3,879,205 and Japanese Patent Publication No. 7561/68, etc.

For the purpose of preventing fog or stabilizing the photographic properties during preparation, storage, and/or photographic processing of the photographic light-sensitive material, a variety of compounds can be present in the photographic emulsions used according to the present invention. For example, a wide variety of compounds which are known as anti-fogging agents or stabilizers, such as azoles, e.g., benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (especially 1-phenyl-5-mercaptotetrazole), etc.; mercaptopyrimidines; mercaptotriazines; thioketo compounds, such as oxazolinethione; azaindenes, e.g., triazaindenes, tetraazaindenes (especially 4-hydroxy-substituted (1,3,3a,7)tetraazaindenes), pentaazaindenes, etc., benzenethiosulfonic acid, benzenesulfinic acid, benzenesulfonic acid amide, etc., can be used. For example, the compounds as described in U.S. Pat. Nos. 3,954,474 and 3,982,947, Japanese Patent Publication No. 28660/77 can be used.

For the purpose of increasing sensitivity, increasing contrast, or accelerating development, the photographic emulsion layers of the photographic light-sensitive material according to the present invention can contain other known additives, such as, for example, polyalkylene oxides or derivatives thereof such as ethers, esters, amines, etc., thioether compounds, thiomorpholine compounds, quaternary ammonium compounds, urethane derivatives, urea derivatives, imidazole derivatives, 3-pyrazolidones, etc. For example, the additives as described in U.S. Pat. Nos. 2,400,532, 2,423,549, 2,716,062, 3,617,280, 3,772,021 and 3,808,003, British Pat. No. 1,488,991, etc. can be employed.

The photographic emulsion used in the present invention can also be spectrally sensitized with methine dyes or other dyes. Suitable spectrally sensitizing dyes which can be employed include cyanine dyes, merocyanine dyes, complex cyanine dyes, complex merocyanine dyes, holopolar cyanine dyes, hemicyanine dyes, styryl dyes, and hemioxonol dyes. Of these dyes, cyanine dyes, merocyanine dyes and complex merocyanine dyes are particularly useful. Any conventionally utilized nucleus for cyanine dyes, such as basic heterocyclic nuclei, is applicable to these dyes. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc., and further, nuclei formed by condensing alicyclic hydrocarbon rings with these nuclei formed by condensing aromatic hydrocarbon rings with these nuclei, that is, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc., are appropriate. The carbon atoms of these nuclei can also be substituted, if desired.

The merocyanine dyes and the complex merocyanine dyes that can be employed contain 5- or 6-membered heterocyclic nuclei such as a pyrazolin-5-one nucleus, a thiohydantoin nucleus, a 2-thioxazolidin-2,4-dione nucleus, a thiazolidin-2,4-dione nucleus, a rhodanine nucleus, a thiobarbituric acid nucleus, and so forth.

Useful sensitizing dyes include those described in German Pat. No. 929,080, U.S. Pat. Nos. 2,231,658, 2,493,748, 2,503,776, 2,519,001, 2,912,329, 3,656,959, 3,672,897, 3,694,217, 4,025,349 and 4,046,572, British Pat. No. 1,242,588, Japanese Patent Publication Nos. 14030/69 and 24844/77, etc.

These sensitizing dyes can be employed individually, and can also be employed in combination. A combination of sensitizing dyes is often used particularly for the purpose of supersensitization. Representative examples thereof are described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281 and 1,507,803, Japanese Patent Publication Nos. 4936/68 and 12375/78, and Japanese Patent Application (OPI) Nos. 110618/77 and 109925/77, etc.

The sensitizing dyes may be present in the emulsion together with dyes which themselves do not give rise to spectrally sensitizing effects but exhibit a supersensitizing effect or materials which do not substantially absorb visible light but exhibit a supersensitizing effect. For example, aminostilbene compounds substituted with a nitrogen-containing heterocyclic group (e.g., those described in U.S. Pat. Nos. 2,933,390 and 3,635,721), aromatic organic acid-formaldehyde condensates (e.g., those described in U.S. Pat. No. 3,743,510), cadmium salts, azaindene compounds, etc., can be present. The combinations as described in U.S. Pat. Nos. 3,615,613, 3,615,641, 3,617,295 and 3,635,721 are particularly useful.

The hydrophilic colloid layers of the photographic light-sensitive material prepared according to the present invention can contain water-soluble dyes such as filter dyes or for purpose of preventing irradiation or other various purposes. Such dyes include oxonol dyes, hemioxonol dyes, styryl dyes, merocyanine dyes, cyanine dyes and azo dyes. Of these dyes, oxonol dyes, hemioxonol dyes and merocyanine dyes are especially useful. Specific examples of these dyes which can be employed are described, for example, in British Pat. Nos. 584,609 and 1,177,429, Japanese Patent application (OPI) Nos. 85130/73, 99620/74, 114420/74 and 108115/77, U.S. Pat. Nos. 2,274,782, 2,533,472, 2,956,879, 3,148,186, 3,177,078, 3,247,127, 3,540,887, 3,575,704, 3,653,905, 3,718,472, 4,071,312 and 4,070,352, etc.

The photographic emulsion layers and other hydrophilic colloid layers of the photographic light-sensitive material prepared in accordance with the present invention can contain whitening agents, such as stilbenes, triazines, oxazoles, or coumarins, etc. These agents can be water-soluble or can also be employed as a dispersion of water-insoluble whitening agents. Specific examples of fluorescent whitening agents are described in U.S. Pat. Nos. 2,632,701, 3,169,840 and 3,359,102, and British Pat. Nos. 852,075 and 1,319,763, etc.

In the practice of the present invention, known color fading preventing agents as described below can be employed. These dye image stabilizers can be used individually or as a combination of two or more thereof. Specific examples of known color fading preventing agents include, for example, hydroquinone derivatives as described in U.S. Pat. Nos. 2,360,290, 2,418,613, 2,675,314, 2,701,197, 2,704,713, 2,728,659, 2,732,300, 2,735,765, 2,710,801 and 2,816,028, British Pat. No. 1,363,921; gallic acid derivatives as described in U.S. Pat. Nos. 3,457,079 and 3,069,262; p-alkoxyphenols as described in U.S. Pat. No. 2,735,765 and 3,698,909, Japanese Patent Publication Nos. 20977/74 and 6623/77; p-oxyphenol derivatives as described in U.S. Pat. Nos. 3,432,300, 3,573,050, 3,574,627 and 3,764,337, Japanese Patent Application (OPI) Nos. 35633/77, 147434/77 and 152225/77; bisphenol derivatives as described in U.S. Pat. No. 3,700,455, etc.

The photographic light-sensitive materials prepared according to the present invention can also contain, as color fog preventing agents, hydroquinone derivatives, aminophenol derivatives, gallic acid derivatives, ascorbic acid derivatives, etc. Specific examples of these agents are described in U.S. Pat. Nos. 2,360,290, 2,336,327, 2,403,721, 2,418,613, 2,675,314, 2,701,197, 2,704,713, 2,728,659, 2,732,300 and 2,735,765, Japanese Patent Application (OPI) Nos. 92988/75, 92989/75, 110337/75 and 146235/77, Japanese Patent Publication No. 23813/75, etc.

The present invention is also applicable to multilayer multicolor photographic materials containing layers sensitive to at least two different spectral wavelength ranges on a support. A multilayer natural color photographic material generally possesses at least one red-sensitive silver halide emulsion layer, at least one green-sensitive silver halide emulsion layer and at least one blue-sensitive silver halide emulsion layer, respectively, on a support. The order of these layers can be varied, if desired. Ordinarily, a cyan forming coupler is present in a red-sensitive silver halide emulsion layer, a magenta forming coupler is present in a green-sensitive silver halide emulsion layer and a yellow forming coupler is present in a blue-sensitive silver halide emulsion layer, respectively. However, if desired, a different combination can be employed.

Known methods can be used for processing the photographic light-sensitive material according to the present invention. Known processing solutions can be used. The processing temperature can be from about 18° C. to about 50° C., in general, but temperatures lower than about 18° C. or higher than about 50° C. may be used, if desired. The photographic light-sensitive materials of the present invention are particularly suitable for high temperature processing at 30° C. or more. Either a development processing for forming silver images (black-and-white photographic processing) or a color photographic processing comprising developing processing for forming dye images can be employed, if desired.

The color developing solution generally comprises an alkaline aqueous solution containing a color developing agent. Suitable color developing agents which can be employed include known primary aromatic amine developing agents, e.g., phenylenediamines (e.g., 4-amino-N,N-diethylaniline, 3-methyl-4-amino-N,N-diethylaniline, 4-amino-n-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfonamidoethylaniline, 4-amino-3-methyl-N-ethyl-N-$\beta$-methoxyethylaniline, etc.).

In addition, developing agents as described in L. F. A. Mason, *Photographic Processing Chemistry,* pages 226 to 229, Focal Press (1966), U.S. Pat. Nos. 2,193,015 and 2,592,364, Japanese Patent Application (OPI) No. 64933/73, etc. can be employed.

The color developing solution can also contain pH buffering agents, such as sulfites, carbonates, borates and phosphates of alkali metals, development inhibitors or antifogging agents such as bromides, iodides or organic antifogging agents, etc. In addition, if desired, the color developing solution can also contain water softeners, predeveloping solution can also contain water softeners, preservatives such as hydroxylamine; organic solvents such as benzyl alcohol, diethylene glycol, etc.; development accelerators such as polyethylene glycol, quaternary ammonium salts, amines; dye forming couplers; competing couplers; fogging agents such as sodium borohydride; auxiliary developing agents such as 1-phenyl-3-pyrazolidone; viscosity-imparting agents; polycarboxylic acid type chelating agents as described in U.S. Pat. No. 4,083,723; anti-oxidizing agents as described in West German Patent Application (OLS) No. 2,622,950, etc.

The photographic emulsion layers after color development are generally subjected to bleach processing. Bleach processing can be performed at the same time as fixing, or separately therefrom. Suitable bleaching agents which can be employed are compounds of polyvalent metals such as iron (III), cobalt (III), chromium (VI), copper (II), etc., peracids, quinones, nitroso compounds, etc. Specific examples include ferricyanides; bichromates; organic complexes of iron (III) or cobalt (III) with aminopolycarboxylic acids such as ethylenediaminetetraacetic acid, nitrilotriacetic acid, 1,3-diamino-2-propanol tetraacetic acid, etc., or organic acids such as citric acid, tartaric acid, malic acid, etc.; persulfates; permanganates; nitrosophenol; etc. Of these, particularly useful bleaching agents are potassium ferricyanide, sodium ethylenediaminetetraacetato iron (III) and ammonium ethylenediaminetetraacetato iron (III). Ethylenediaminetetraacetato iron (III) complex is useful both in a bleaching solution and in a mono both bleach-fixing solution.

Bleaching solutions and bleach-fixing solutions can contain various additives, including bleach accelerating agents as described in U.S. Pat. Nos. 3,042,520 and 3,241,966, Japanese Patent Publication Nos. 8506/70 and 8836/70, thiol compounds as described in Japanese Patent Application (OPI) No. 65732/78, etc.

The present invention is explained in greater detail with reference to the following examples, but the present invention should not to be construed as being limited thereto. Again, unless otherwise indicated, all parts, percents, ratios are by weight.

EXAMPLE 1

10 g of Coupler (3) according to the present invention was dissolved by heating in a mixture of 5 ml of dibutyl phthalate and 10 ml of ethyl acetate and the resulting solution was mixed with 100 ml of a 10% aqueous solution of gelatin containing 0.1 g of sodium dodecylbenzenesulfonate. The mixture was stirred at 50° C. using a homogenizer rotating with high speed to obtain a coupler dispersion. The dispersion was mixed with 150 g of a silver chlorobromide emulsion, to which were added 15 ml of a 2% aqueous solution of 2-hydroxy-4,6-dichloro-s-triazine sodium salt and 6 ml of a 5% aqueous solution of saponin, and the resulting mixture was coated on a cellulose acetate film in a silver coated amount of 1 g/m$^2$. On the emulsion layer a gelatin protective layer was coated at a dry thickness of 1$\mu$ to prepare Sample A. Further, Samples B to R were prepared in the same manner as described for Sample A except using the couplers as shown in Table 1 below in place of Coupler (3) and adjusting a coated molar amount of coupler and a coated amount of silver to those of Sample A.

Samples A to R were exposed stepwise to light for sensitometry and then subjected to the following development processing.

| Step | Temperature (°C.) | Time |
|---|---|---|
| Color Development | 38 | 3 min |
| Washing with Water | 38 | 1 min |
| Bleach-Fixing | 38 | 1 min 30 sec |
| Washing with water | 38 | 1 min |

The compositions of the color developing solutions used were as follows.

| | CD-1 | CD-2 | CD-3 |
|---|---|---|---|
| Benzyl Alcohol | — | — | 15 ml |
| Diethylene Glycol | — | — | 8 ml |
| Developing Agent | A*: 3.5 g | B*: 5 g | B*: 5 g |
| Sodium Sulfite | 2 g | 2 g | 2 g |
| Hydroxylamine Sulfate | 3 g | 3 g | 3 g |
| Potassium Carbonate | 30 g | 30 g | 30 g |
| Water to make | 1 l | 1 l | 1 l |
| pH (adjusted to) | 10.2 | 10.2 | 10.2 |

A*: 4-Amino-3-methyl-N—ethyl-N—$\beta$-hydroxyethylaniline Sulfate
B*: 4-Amino-3-methyl-N—ethyl-N—$\beta$-(methanesulfonamido)-ethylaniline Sulfate The composition of the bleach-fixing solution used was as follows.
Disodium Ethylenediaminetetraacetate: 2 g
Ferric Ethylenediaminetetraacetate: 40 g
Sodium Sulfite: 5 g
Ammonium Thiosulfate: 70 g
Water to make: 1 l
pH was adjusted to: 6.8

The transparent density of each sample thus-processed was measured (cyan, magenta or yellow density was measured depending on the dye formed) and the maximum density (Dmax) and gamma (γ) were determined. The results obtained are shown in Table 1 below.

TABLE 1

| Sample | Coupler | CD-1 Dmax | CD-1 γ | CD-2 Dmax | CD-2 γ | CD-3 Dmax | CD-3 γ |
|---|---|---|---|---|---|---|---|
| A | Coupler (3) [Present Invention] | 3.48 | 2.59 | 3.41 | 2.54 | 3.42 | 2.54 |
| B | Coupler (4) [Present Invention] | 3.50 | 2.51 | 3.39 | 2.56 | 3.52 | 2.56 |
| C | Coupler (9) [Present Invention] | 3.38 | 2.52 | 3.35 | 2.50 | 3.41 | 2.54 |
| D | CR-1 [Comparison] | 2.80 | 1.88 | 2.23 | 1.43 | 2.78 | 1.90 |
| E | CR-2 [Comparison] | 2.65 | 1.49 | 2.13 | 1.27 | 2.68 | 1.52 |
| F | CR-3 [Comparison] | 3.01 | 2.00 | 2.83 | 1.91 | 3.12 | 2.12 |
| G | Coupler (7) [Present Invention] | 3.52 | 2.55 | 3.32 | 2.51 | 3.55 | 2.49 |
| H | Coupler (10) [Present Invention] | 3.85 | 2.63 | 3.62 | 2.66 | 3.82 | 2.61 |
| I | Coupler (14) [Present Invention] | 3.40 | 2.51 | 3.21 | 2.40 | 3.41 | 2.52 |
| J | MR-1 [Comparison] | 2.93 | 2.03 | 2.78 | 1.92 | 3.16 | 2.12 |
| K | MR-2 [Comparison] | 3.03 | 2.09 | 2.88 | 1.95 | 3.09 | 2.10 |
| L | MR-3 [Comparison] | 3.15 | 2.17 | 3.06 | 2.03 | 3.21 | 2.15 |
| M | Coupler (1) [Present Invention] | 3.18 | 2.21 | 3.05 | 2.01 | 3.15 | 2.20 |
| N | Coupler (2) [Present Invention] | 3.30 | 2.31 | 3.12 | 2.13 | 3.30 | 2.29 |
| O | Coupler (5) [Present Invention] | 3.25 | 2.13 | 3.08 | 2.08 | 3.21 | 2.12 |
| P | YR-1 [Comparison] | 3.01 | 1.98 | 2.64 | 1.57 | 2.99 | 1.95 |
| Q | YR-2 [Comparison] | 2.80 | 1.43 | 2.15 | 1.21 | 2.79 | 1.55 |
| R | YR-3 [Comparison] | 3.03 | 2.01 | 2.78 | 1.72 | 3.05 | 2.02 |

The composition couplers used were as follows:

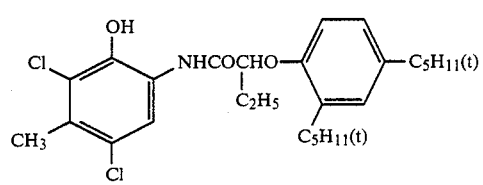

CR-1

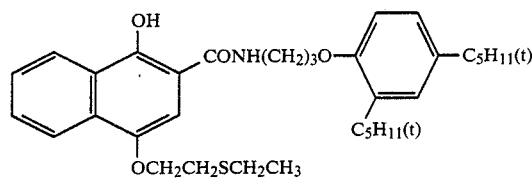

CR-2

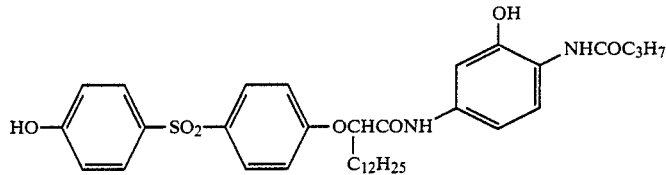

CR-3

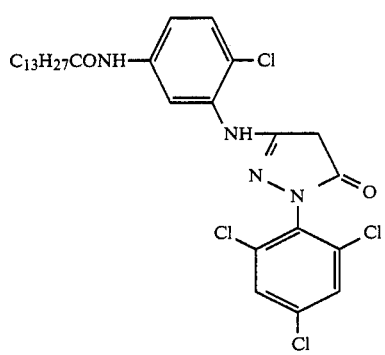

MR-1

-continued
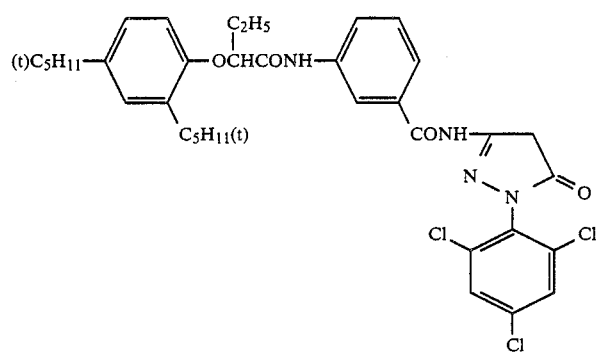
MR-2
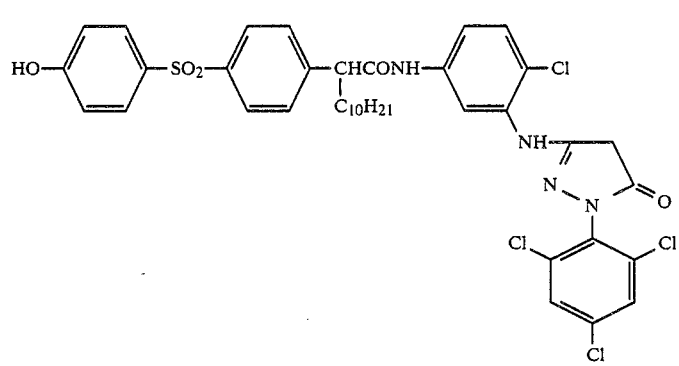
MR-3
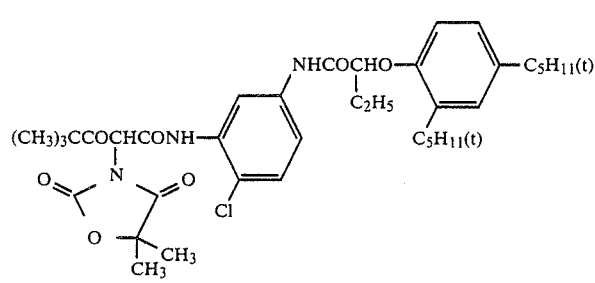
YR-1
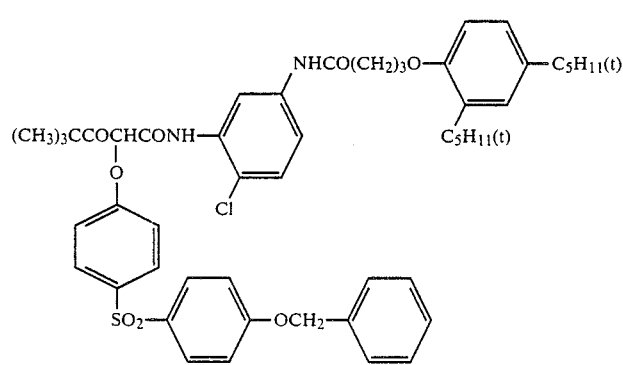
YR-2

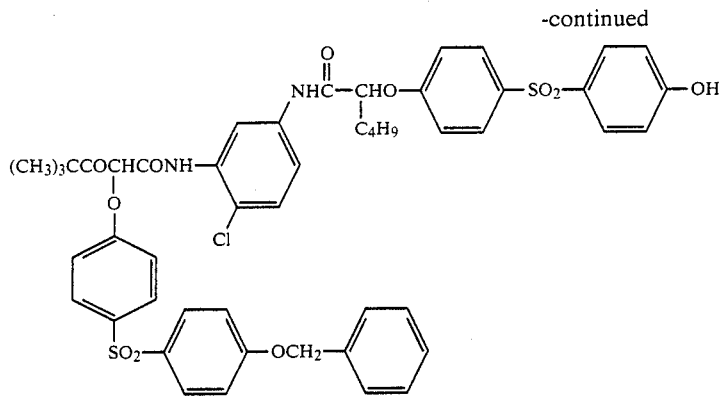
YR-3

From the results shown in Table 1 above, it is apparent that Samples A to C, G to I and M to O containing the coupler according to the present invention exhibit excellent color forming properties while Dmax and γ are low and thus inferior color forming properties are obtained in Samples D to F, J to L and P to R for comparison. In particular, when the results obtained with color developer CD-2 and those obtained with color developer CD-3 both of which contain the common color developing agent having a relatively high activity are compared, the comparison samples exhibit a marked decrease in color forming properties with color developer CD-2 which does not contain benzyl alcohol. On the contrary, in the samples according to the present invention the differences of the results between color developers CD-2 and CD-3 are small and they provide sufficiently high color densities without using benzyl alcohol.

EXAMPLE 2

On a paper support, both surfaces of which were laminated with polyethylene, were coated a first layer (undermost layer) to a sixth layer (uppermost layer) as shown in Table 2 below in order to prepare color photographic light-sensitive materials which are designated Samples A to C.

The coating solution for the first layer was prepared in the following manner. That is, 100 g of the yellow coupler shown in Table 2 below was dissolved in a mixture of 166.7 ml of dibutyl phthalate (DBP) and 200 ml of ethyl acetate and the resulting solution was dispersed in 800 g of a 10% aqueous solution of gelatin containing 80 ml of a 1% aqueous solution of sodium dodecylbenzenesulfonate. The dispersion was mixed with 1450 g of a blue-sensitive silver chlorobromide emulsion (containing 66.7 g of silver and having a bromide content of 80% by mol) to prepare a coating solution. Coating solutions for other layers were prepared in a similar manner. 2,4-Dichloro-6-hydroxy-s-triazine sodium salt was used as a hardener in each layer.

The following spectral sensitizing dyes were employed in the emulsion layers, respectively.

Blue-Sensitive Emulsion Layer:
Sodium salt of 3,3'-di-(γ-sulfopropyl)selenacyanine: $2 \times 10^{-4}$ mol per mol of silver halide Green-Sensitive Emulsion Layer:
Sodium salt of 3,3'-di-(γ-sulfopropyl)-5,5'-diphenyl-9-ethyloxacarbocyanine: $2.5 \times 10^{-4}$ mol per mol of silver halide Red-Sensitive Emulsion Layer:
Sodium salt of 3,3'-di-(γ-sulfopropyl)-9-methyl-thiadicarbocyanine: $2.5 \times 10^{-4}$ mol per mol of silver halide The following dyes were employed as irradiation preventing dyes in the emulsion layers, respectively.

Green-Sensitive Emulsion Layer:

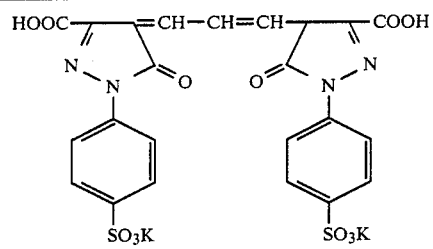

Red-Sensitive Emulsion Layer:

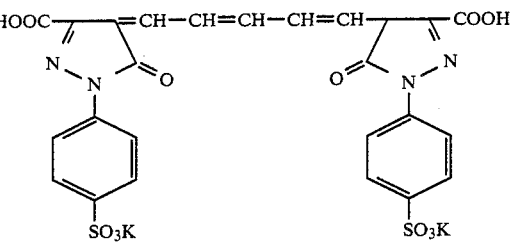

The chemical structures of the solvents set forth in Table 2 are as follows

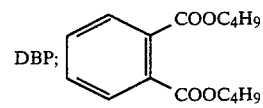

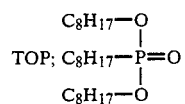

TABLE 2

| | | Sample No. | | |
|---|---|---|---|---|
| | | A | B | C |
| Sixth Layer: (protective layer) | Gelatin Coating amount | 1500 mg/m² | 1500 mg/m² | 1500 mg/m² |

TABLE 2-continued

| | | Sample No. | | |
|---|---|---|---|---|
| | | A | B | C |
| Fifth Layer: (red-sensitive layer) | Silver Chlorobromide Emulsion (silver bromide: 50 mol %) | | | |
| | Coating amount of silver | 300 mg/m² | 300 mg/m² | 300 mg/m² |
| | Cyan Coupler | CR - 1 [Comparison] | Coupler (16) [Present Invention] | Coupler (23) [Present Invention] |
| | Coating amount | 400 mg/m² | 570 mg/m² | 640 mg/m² |
| | Solvent | DBP | DBP | DBP |
| | Coating amount | 240 mg/m² | 340 mg/m² | 380 mg/m² |
| Fourth Layer: (ultraviolet ray absorbing layer) | Gelatin Coating amount | 2000 mg/m² | 2000 mg/m² | 2000 mg/m² |
| | Ultraviolet Light Absorbing Agent | UV-1: 15 mg/m² UV-2: 45 mg/m² UV-3: 90 mg/m² | UV-1: 15 mg/m² UV-2: 45 mg/m² UV-3: 90 mg/m² | UV-1: 15 mg/m² UV-2: 45 mg/m² UV-3: 90 mg/m² |
| | Coating amount Solvent | DBP | DBP | DBP |
| | Coating amount | 60 mg/m² | 60 mg/m² | 60 mg/m² |
| Third Layer: (green-sensitive layer) | Silver Chlorobromide Emulsion (silver bromide: 70 mol %) | | | |
| | Coating amount of silver | 450 mg/m² | 450 mg/m² | 450 mg/m² |
| | Magenta Coupler | MR - 1 [Comparison] | Coupler (18) [Present Invention] | Coupler (21) [Present Invention] |
| | Coating amount | 350 mg/m² | 490 mg/m² | 470 mg/m² |
| | Solvent | TOP | TOP | TOP |
| | Coating amount | 440 mg/m² | 620 mg/m² | 590 mg/m² |
| Second Layer: (intermediate layer) | Gelatin Coating amount | 1500 mg/m² | 1500 mg/m² | 1500 mg/m² |
| First Layer: (blue-sensitive layer) | Silver Chlorobromide Emulsion (silver bromide: 80 mol %) | | | |
| | Coating amount of silver | 1500 mg/m² | 1500 mg/m² | 1500 mg/m² |
| | Yellow Coupler | YR - 1 [Comparison] | Coupler (13) [Present Invention] | Coupler (15) [Present Invention] |
| | Coating amount | 600 mg/m² | 730 mg/m² | 590 mg/m² |
| | Solvent | DBP | DBP | DBP |
| | Coating amount | 1000 mg/m² | 1220 mg/m² | 980 mg/m² |
| Support | Paper support, both surfaces of which were laminated with polyethylene | | | |

Each sample was exposed stepwise to light for sensitometry and then subjected to the same development processing as described in Example 1 except that color developers CD-2 and CD-3 were employed as color developing solutions. The reflection densities of each sample thus-processed were measured (with red light, green light and blue light) and the fog, maximum density (Dmax) and gamma ($\gamma$) were determined. The results obtained are shown in Table 3 below.

UV-1, UV-2 and UV-3 shown in Table 2 above are the compounds having the following structures, respectively.

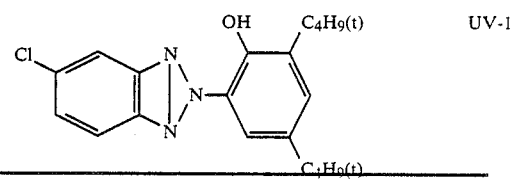

UV-1

TABLE 3

| Sample | CD-2 | | | | | | | | | CD-3 | | | | | | | | |
|---|---|---|---|---|---|---|---|---|---|---|---|---|---|---|---|---|---|---|
| | Cyan | | | Magenta | | | Yellow | | | Cyan | | | Magenta | | | Yellow | | |
| | Fog | $\gamma$ | Dmax | Fog | $\gamma$ | Dmax | Fog | $\gamma$ | Dmax | Fog | $\gamma$ | Dmax | Fog | $\gamma$ | Dmax | Fog | $\gamma$ | Dmax |
| A | 0.08 | 2.78 | 2.12 | 0.07 | 2.82 | 2.23 | 0.09 | 2.84 | 2.14 | 0.10 | 3.23 | 2.58 | 0.08 | 3.39 | 2.72 | 0.12 | 3.10 | 2.69 |
| B | 0.08 | 3.25 | 2.63 | 0.07 | 3.39 | 2.72 | 0.09 | 3.39 | 2.69 | 0.10 | 3.40 | 2.71 | 0.08 | 3.46 | 2.89 | 0.12 | 3.41 | 2.89 |
| C | 0.08 | 3.40 | 2.71 | 0.07 | 3.38 | 2.69 | 0.08 | 3.40 | 2.70 | 0.10 | 3.43 | 2.78 | 0.08 | 3.43 | 2.80 | 0.12 | 3.42 | 2.77 |

From the results shown in Table 3 above, it is apparent that Samples B and C according to the present invention provide excellent color forming properties using color developer CD-2, although in Sample A for comparison, $\gamma$ and Dmax are remarkably decreased when color developer CD-2, which is a color developing solution that does not contain benzyl alcohol, was used.

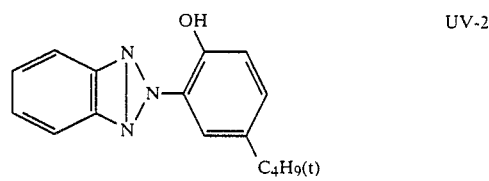

UV-2

-continued

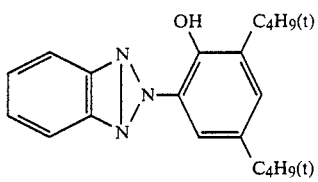

UV-3

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material comprising a support having thereon at least one silver halide emulsion layer, the color photographic light-sensitive material containing a coupler having a group represented by the general formula (I)

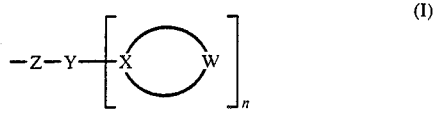

(I)

wherein W represents

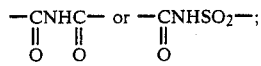

X represents an organic residue necessary for forming a 5-membered or 6-membered nitrogen-containing heterocyclic ring or a condensed ring thereof together with W; Y represents an organic residue connecting Z and X and containing at least one carbon atom which is bonded to Z; Z represents an oxygen atom or a sulfur atom; and n represents an integer of 1 to 2; at the coupling position of the coupler.

2. The silver halide color photographic light-sensitive material as claimed in claim 1, wherein the coupler is represented by the following general formula (II):

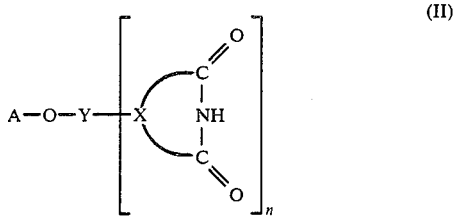

(II)

wherein A represents a coupler residue in which a hydrogen atom at the coupling position is eliminated; X represents an organic residue necessary for forming a 5-membered or 6-membered nitrogen-containing heterocyclic ring or a condensed ring thereof together with the moiety of the formula

Y represents an organic residue connecting O and X and containing at least one carbon atom which is bonded to O; and n represents an integer of 1 or 2.

3. The silver halide color photographic light-sensitive material as claimed in claim 2, wherein the coupler contains a diffusion-resistant group in any of the groups represented by A, Y and X.

4. The silver halide color photographic light-sensitive material as claimed in claim 2, wherein A represents as a yellow color forming coupler residue, a pivaloyl acetanilide residue, a benzoyl acetanilide residue, a malonic diester residue, malondiamide residue, a dibenzoylmethane residue, a benzothiazolyl acetamide residue, a malonic ester monoamide residue, a benzothiazolyl acetate residue, a benzoxazolyl acetamide residue, a benzoxazolyl acetate residue, a benzimidazolyl acetamide residue or a benzimidazolyl acetate residue.

5. A silver halide color photographic light-sensitive material as claimed in claim 2, wherein A represents, as a magenta color forming coupler residue, a 5-oxo-2-pyrazoline residue, a pyrazolobenzimidazole residue, pyrazolotriazole residue, a cyanoacetophenone residue or a pyrazoloimidazole residue.

6. The silver halide color photographic light-sensitive material as claimed in claim 2, wherein A represents, as a cyan color forming coupler residue, a phenol residue type or α-naphthol residue.

7. The silver halide color photographic light-sensitive material as claimed in claim 2, wherein A represents, as a non-color forming coupler residue, an indanone residue or an acetophenone residue.

8. The silver halide color photographic light-sensitive material as claimed in claim 2, wherein the 5-membered or 6-membered nitrogen-containing heterocyclic ring formed with the organic residue represented by X is a 2,4-dioxoimidazolidine ring, a 2,4-dioxo-1,3-oxazolidine ring, a 3,5-dioxo-1,2,4-triazolidine ring, a phthalimide ring, a succinimide ring, an uracil ring, a glycolimide ring, a xanthene ring, a glutarimide ring, a parabanic acid ring, a 2,6-dioxo-1,2,3,6-tetrahydropyrimidine ring, a urazole ring, a barbituric acid ring or a 2,4-dioxo-1,3-thiazolidine ring.

9. The silver halide color photographic light-sensitive material as claimed in claim 8, wherein the 5-membered or 6-membered nitrogen-containing heterocyclic ring formed with the organic residue represented by X is substituted with an alkyl group, a phenyl group, a halogen atom, an aralkyl group, an alkoxy group, a carboxy group, an acylamino group, an alkoxycarbonyl group, a cyano group, a nitro group, an alkylsulfonamido group, an arylsulfonamido group, a hydroxy group, an alkylthio group, an arylthio group, an imido group, an alkylsulfonyl group, an arylsulfonyl group, a sulfamoyl group which may be substituted with an alkyl group or an aryl group, a sulfamoyl group which may be substituted with an alkyl group or an aryl group, a carbamoyl group which may be substituted with an alkyl group or an aryl group, a ureido group which may be substituted with an alkyl group or an aryl group, an amino group which may be substituted with an alkyl group or an aryl group or a urethane group which may be substituted with an alkyl group or an aryl group.

10. The silver halide color photographic light-sensitive material as claimed in claim 2, wherein Y represents an aliphatic group, an aromatic group, two or more these groups combined through an ether bond, a thioether bond, an ester bond, an amido bond, a sulfone bond, a sulfoxide bond, a sulfonamido bond, an azo bond, an imido bond, a ureido bond, an amino bond, a urethane bond, an imino bond, a hydrazo bond or a sulfamido bond, or a combination of one of these groups with one of the above described bonds connected to X.

11. The silver halide color photographic light-sensitive material as claimed in claim 2, wherein A represents a coupler residue represented by the following general formula (III) or (IV):

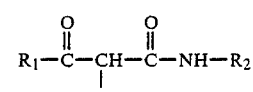  (III)

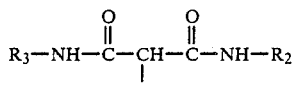  (IV)

wherein $R_1$ represents an aliphatic group, an aromatic group, an alkoxy group or a heterocyclic group; and $R_2$ and $R_3$ each represents an aromatic group or a heterocyclic group.

12. The silver halide color photographic light-sensitive material as claimed in claim 11, wherein the aliphatic group represented by $R_1$ is an alkyl group which may be substituted with a substituent selected from the group consisting of an alkoxy group, an aryloxy group, an amino group, an acylamino group and a halogen atom.

13. The silver halide color photographic light-sensitive material as claimed in claim 11, wherein the aromatic group represented by $R_1$, $R_2$ or $R_3$ is a phenyl group which may be substituted with a substituent selected from the group consisting of an alkyl group, an alkenyl group, an alkoxy group, an alkoxycarbonyl group, an alkoxycarbonylamino group, an aliphatic amido group, an alkylsulfamoyl group, an alkylsulfonamido group, an alkylureido group, an alkyl-substituted succinimido group, each containing 32 or less carbon atoms, an aryloxy group, an aryloxycarbonyl group, an arylcarbamoyl group, an arylamido group, an arylsulfamoyl group, an arylsulfonamido group, an arylureido group, an amino group, a hydroxy group, a carboxy group, a sulfo group, a nitro group, a cyano group, a thiocyano group and a halogen atom.

14. The silver halide color photographic light-sensitive material as claimed in claim 11, wherein the aromatic group represented by $R_1$, $R_2$ or $R_3$ is a naphthyl group, a quinolyl group, an isoquinolyl group, a chromanyl group, a coumaranyl group or a tetrahydronaphthyl group.

15. The silver halide color photographic light-sensitive material as claimed in claim 11, wherein the alkoxy group represented by $R_1$ is an alkoxy group in which the alkyl moiety is a straight chain or branched chain alkyl group having from 1 to 32 carbon atoms; an alkenyl group; a cyclic alkyl group; or a cyclic alkenyl group; each of which may be substituted with a substituent selected from the group consisting of a halogen atom, an aryl group and an alkoxy group.

16. The silver halide color photographic light-sensitive material as claimed in claim 11, wherein the heterocyclic group represented by $R_1$, $R_2$ or $R_3$ is a group derived from a heterocyclic ring selected from the group consisting of thiophene, furan, pyran, pyrrole, pyrazole, pyridine, pyrazine, pyrimidine, pyridazine, indolizine, imidazole, thiazole, oxazole, triazine, thiadiazole and oxazine rings.

17. The silver halide color photographic light-sensitive material as claimed in claim 2, wherein A represents a coupler residue represented by the following general formula (V), (VI), (VII) or (VIII):

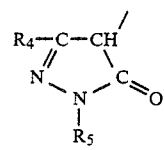  (V)

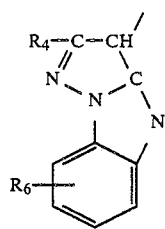  (VI)

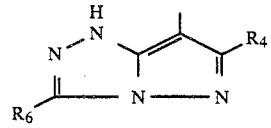  (VII)

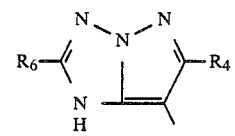  (VIII)

wherein $R_5$ represents a straight chain or branched chain alkyl group having from 1 to 32 carbon atoms, an alkenyl group, a cyclic alkyl group, an aralkyl group or a cyclic alkenyl group, each of which may be substituted with a substituent selected from the group consisting of a halogen atom, a nitro group, a cyano group, an aryl group, an alkoxy group, an aryloxy group, a carboxy group, an alkylthiocarbonyl group, an arylthiocarbonyl group, an alkoxycarbonyl group, an aryloxycarbonyl group, a sulfo group, a sulfamoyl group, a carbamoyl group, an acylamino group, a diacylamino group, a ureido group, a urethane group, a thiourethane group, a sulfonamido group, a heterocyclic group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxy group and a mercapto group; an aryl group which may be substituted with a substituent selected from the group consisting of an alkyl group, an alkenyl group, a cyclic alkyl group, an aralkyl group, a cyclic alkenyl group, a halogen atom, a nitro group, a cyano group, an aryl group, an alkoxy group, an aryloxy group, a carboxy group, an alkoxycarbonyl group, an aryloxycarbonyl group, a sulfo group, a sulfamoyl group, a carbamoyl group, an acylamino group, a diacylamino group, a ureido group, a urethane group, a sulfonamido group, a heterocyclic group, an arylsulfonyl group, an alkylsulfonyl group, an arylthio group, an alkylthio group, an alkylamino group, a dialkylamino group, an anilino group, an N-alkylanilino group, an N-arylanilino group, an N-acylanilino group, a hydroxy group and a mercapto group; a heterocyclic group which may be substituted with a substituent selected from the group consisting of substituents as defined for the aryl group described above; an aliphatic acyl group; an aromatic acyl group; alkylsulfonyl group; an arylsulfonyl group; an alkylcarbamoyl group; an arylcarbamoyl group; an alkylthiocarbamoyl group; or an arylthiocarbamoyl group; $R_4$ represents a hydrogen atom; a straight chain or branched chain alkyl group having from 1 to 32 carbon atoms, an alkenyl group, a cyclic alkyl group, an aralkyl group, a cyclic alkenyl group, an aryl group or a heterocyclic group, each of which may be substituted with a substituent selected from the group consisting of substituents as defined for these groups for $R_5$ respectively; an alkoxycarbonyl group; an aryloxycarbonyl group; an aralkyloxycarbonyl group; an alkoxy group; an aryloxy group; an alkylthio group; an arylthio group; a carboxy group; an acylamino group; a diacylamino group; an N-alkylacylamino group; an N-arylacylamino group; a ureido group; a urethane group; a thiourethane group; an arylamino group; an alkylamino group; a cycloamino group; a heterocyclic amino group; an alkylcarbonyl group; an arylcarbonyl group; a sulfonamido group; a carbamoyl group; a sulfamoyl group; a cyano group; a hydroxy group; a mercapto group; a halogen atom; or a sulfo group; and $R_6$ represents a hydrogen atom; a straight chain or branched chain alkyl group having from 1 to 32 carbon atoms, an alkenyl group, a cyclic alkyl group, an aralkyl group, a cyclic alkenyl group, an aryl group or a heterocyclic group, each of which may be substituted with a substituent selected from the group consisting of substituents as defined for these groups for $R_5$ respectively; a cyano group; an alkoxy group, an aryloxy group, a halogen atom, a carboxy group, an alkoxycarbonyl group, an aryloxycarbonyl group, an acyloxy group, a sulfo group, a sulfamoyl group, a carbamoyl group, an acylamino group, a diacylamino group, a ureido group, a urethane group, a sulfonamido group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxy group or a mercapto group.

18. The silver halide color photographic light-sensitive material as claimed in claim 17, wherein $R_5$ represents a phenyl group which is substituted with an alkyl group, an alkoxy group or a halogen atom, at at least one of the o-positions thereof.

19. The silver halide color photographic light-sensitive material as claimed in claim 2, wherein A represents a coupler residue represented by the following general formula (IX), (X), (XI) or (XII):

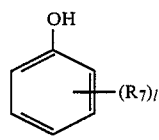 (IX)

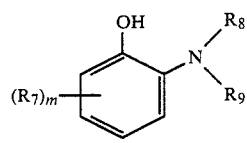 (X)

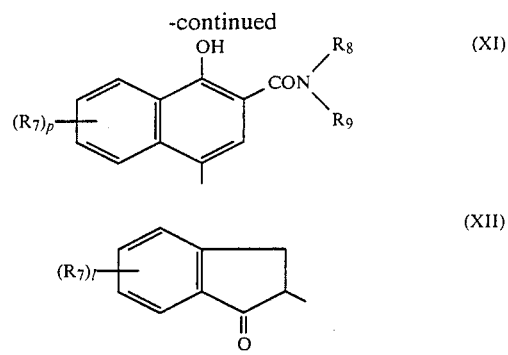

wherein $R_7$ represents a hydrogen atom, a halogen atom, an alkoxycarbonylamino group, an aliphatic hydrocarbon residue, an N-arylureido group, an acylamino group, an —O—$R_{12}$ group or an —S—$R_{12}$ group, wherein $R_{12}$ represents an aliphatic hydrocarbon residue; $R_8$ and $R_9$ each represents an aliphatic hydrocarbon residue, an aryl group or a heterocyclic group, one of $R_8$ and $R_9$ may be a hydrogen atom, or $R_8$ and $R_9$ may combine and form a nitrogen-containing heterocyclic nucleus; l represents an integer of 1 to 4; m represents an integer of 1 to 3; and p represents an integer of 1 to 5.

20. The silver halide color photographic light-sensitive material as claimed in claim 19, wherein the aliphatic hydrocarbon group, the aryl group or the heterocyclic group represented by $R_7$, $R_8$ or $R_9$ may be substituted with a substituent selected from the group consisting of a halogen atom, a nitro group, a hydroxy group, a carboxy group, an amino group, a substituted amino group, a sulfo group, an alkyl group, an alkenyl group, an aryl group, a heterocyclic group, an alkoxy group, an aryloxy group, an arylthio group, an arylazo group, an acylamino group, a carbamoyl group, an ester group, an acyl group, an acyloxy group, a sulfonamido group, a sulfamoyl group, a sulfonyl group and a morpholino group.

21. The silver halide color photographic light-sensitive material as claimed in claim 2, wherein A represents a coupler residue represented by the following general formula (XIII):

 (XIII)

wherein $R_{10}$ represents an alkanoyl group having from 2 to 32 carbon atoms, an arylcarbamoyl group, an alkylcarbamoyl group having from 2 to 32 carbon atoms, an alkoxycarbonyl group having from 1 to 32 carbon atoms or an aryloxycarbonyl group, each of which may be substituted with a substituent selected from the group consisting of an alkoxy group, an alkoxycarbonyl group, an acylamino group, an alkylsulfamoyl group, an alkylsulfonamido group, an alkylsuccinimido group, a halogen atom, a nitro group, a carboxy group, a cyano group, an alkyl group and an aryl group; and $R_{11}$ represents an arylcarbonyl group, an alkanoyl group having from 2 to 32 carbon atoms, an arylcarbamoyl group; an alkylcarbamoyl group having from 2 to 32 carbon atoms, an alkoxycarbonyl group having from 1 to 32 carbon atoms, an aryloxycarbonyl group, an alkylsulfonyl group having from 1 to 32 carbon atoms, an arylsulfonyl group, an aryl group or a 5-membered or 6-membered heterocyclic group each of which may be substituted with a substituent selected from the group consisting of substituents as defined for $R_{10}$.

22. The silver halide color photographic light-sensitive material as claimed in claim 11, wherein A represents a coupler residue represented by the general formula (III), wherein $R_1$ is a tert-butyl group and $R_2$ is an aromatic group.

23. The silver halide color photographic light-sensitive material as claimed in claim 2, wherein the linking group represented by Y is a group which contains a phenylene group, a carbon atom of which is bonded to the oxygen atom which is in turn attached to the coupling position of the coupler.

24. The silver halide color photographic light-sensitive material as claimed in claim 23, wherein the group containing a phenylene group further contains an aliphatic residue, an aromatic residue, an ether bond, an ester bond, a sulfone bond, a sulfonamido bond, an amido bond, a sulfamido bond or a ureido bond in the bonding connected to X.

25. The silver halide color photographic light-sensitive material as claimed in claim 1, wherein the coupler is present in a silver halide emulsion layer.

26. The silver halide color photographic light-sensitive material as claimed in claim 25, wherein the coupler is present in the silver halide emulsion layer in an amount ranging from $2 \times 10^{-3}$ mol to $5 \times 10^{-1}$ mol per mol of silver in the silver halide emulsion layer.

27. The silver halide color photographic light-sensitive material as claimed in claim 2, wherein the photographic light-sensitive material contains at least one red-sensitive silver halide emulsion layer containing a cyan color forming coupler, at least one green-sensitive silver halide emulsion layer containing a magenta color forming coupler and at least one blue-sensitive silver halide emulsion layer containing a yellow color forming coupler and at least one of these cyan, magenta and yellow color forming couplers is a coupler represented by the general formula (II).

28. A method of forming a color image comprising developing an imagewise exposed silver halide color photographic light-sensitive material comprising a support having thereon at least one silver halide emulsion layer, the color photographic light-sensitive material containing a coupler having a group represented by the general formula (I).

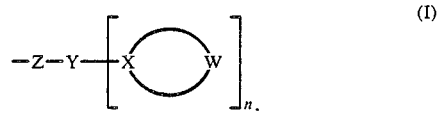

wherein W represents

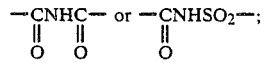

X represents an organic residue necessary for forming a 5-membered or 6-membered nitrogen-containing heterocyclic ring or a condensed ring thereof together with W; Y represents an organic residue connecting Z and X and containing at least one carbon atom which is bonded to Z; Z represents an oxygen atom or a sulfur atom; and n represents an integer of 1 to 2; at the coupling position of the coupler with an aqueous alkaline developing solution containing an aromatic primary amine developing agent.

29. The method of forming a color image as claimed in claim 28, wherein the aqueous alkaline developing solution is free of benzyl alcohol.

* * * * *